(12) United States Patent
Raveendranath et al.

(10) Patent No.: US 6,242,605 B1
(45) Date of Patent: Jun. 5, 2001

(54) ARYLOXY-ALKYL-DIALKYLAMINES

(75) Inventors: Panolil Raveendranath, Monroe; Joseph Zeldis; Galina Vid, both of New City; John R. Potoski, West Nyack, all of NY (US); Jianxin Ren, Tenafly, NJ (US); Silvio Iera, Montreal (CA)

(73) Assignee: American Home Products Corporation, Madison, NJ (US)

( * ) Notice: Subject to any disclaimer, the term of this patent is extended or adjusted under 35 U.S.C. 154(b) by 0 days.

(21) Appl. No.: 09/458,316

(22) Filed: Dec. 10, 1999

Related U.S. Application Data

(62) Division of application No. 09/161,653, filed on Sep. 28, 1998, now Pat. No. 6,005,102.
(60) Provisional application No. 60/090,099, filed on Oct. 15, 1997.

(51) Int. Cl.$^7$ .................. C07D 237/02; C07D 239/02; C07D 241/02; C07C 255/50

(52) U.S. Cl. .................. 546/221; 544/334; 544/336; 546/240; 546/202; 558/419; 540/609

(58) Field of Search ................... 544/224, 336, 544/334, 335; 546/221, 240, 202; 558/419; 564/340

(56) References Cited

U.S. PATENT DOCUMENTS

| | | |
|---|---|---|
| 1,754,678 | 4/1930 | Hahl . |
| 2,133,779 | 10/1938 | Clifford . |
| 3,459,799 | 8/1969 | Gutmann et al. . |
| 4,943,572 | 7/1990 | von Angerer . |
| 5,023,254 | 6/1991 | von Angerer . |
| 5,124,335 | 6/1992 | Patchett et al. . |
| 5,231,092 | 7/1993 | Lavastre et al. . |
| 5,296,596 | 3/1994 | Lavastre et al. . |
| 5,391,735 | 2/1995 | Melloni et al. . |
| 5,496,844 | 3/1996 | Inai et al. . |
| 5,929,097 | * 7/1999 | Levin et al. ............ 514/351 |

FOREIGN PATENT DOCUMENTS

| | | |
|---|---|---|
| 0428312 | 5/1991 | (EP) . |
| 0639567 | 2/1995 | (EP) . |
| 9310741 | 6/1993 | (WO) . |
| 9517383 | 6/1995 | (WO) . |
| 9603375 | 2/1996 | (WO) . |
| 9800137 | 1/1998 | (WO) . |
| 9838163 | 9/1998 | (WO) . |
| 9848797 | 11/1998 | (WO) . |

OTHER PUBLICATIONS

Woessner et al., FASEB J., 1991, 5, 2145.
Birkedal–Hansen et al., Crit. Rev. Oral Biol. Med., 1993, 4, 197.
Cawston, Pharmacol. Ther. 1996, 70, 163.
Powell et al., Cur. Top. Microbiol. and Immunol., 1996, 213, 1.
Dean, Sem. Arthritis Rheum., 1991, 20, 2.
Crawford, H.C et al., Invasion Metast., 1994–95, 14, 234.
Kmonicek et al., Collection of Czechoslovak Chemical Communications, vol. 55, 1990, pp. 1602–1612.
Cossey et al., Journal of the Chemical Society, pp. 954–973, 1965.
Rudinger–Adler et al., Arzneimittel Forschung Drug Research, vol. 29, No. 4, 1979, pp. 591–594.
Marson et al., Chemical Abstracts, vol. 54, No. 2, Jan. 1960.
Ray, et al., Exp. Opin. Invest. Drugs, 1996, 5, 323.
Chem. Abstract, 1965, 62, 7698.
Sharpe et al., J. Med. Chem., 1972, 15, 523.
Jones et al., J. Med. Chem. 1984, 27, 1057.
Huang et al., J. Med. Chem., 1990, 33, 1194.
Howell et al., Arthiritis and Allied Conditions, Phila., 1993, 12$^{th}$ Ed. vol. 2, p. 1723.
Biberger et al., J. Steroid Biochem. Molec. Biol., vol. 58, No. 1, pp. 31–43, 1996.
von Angerer et al., J. Med. Chem. 1987, 30, 131–136.
von Angerer et al., J. Med. Chem., 1990, 33, 2635–2640.
Bone, vol. 17, No. 4, Oct., 1995, pp. 181S–190S.

\* cited by examiner

Primary Examiner—Floyd D. Higel
Assistant Examiner—Ebenezer Sackey
(74) Attorney, Agent, or Firm—Steven R. Eck

(57) ABSTRACT

The present invention provides compounds useful in the synthesis of biologically active compounds, and processes for their production, the compounds having the formula:

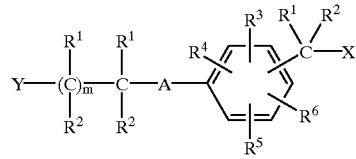

wherein: $R^1$ and $R^2$ are, independently, selected from H; $C_1$–$C_{12}$ alkyl or $C_1$–$C_6$ perfluorinated alkyl; X represents a leaving group; A is 0 or S; m is an integer from 1 to 3, preferably 2; $R^3$, $R^4$, $R^5$, and $R^6$ are independently selected from H, halogen, —$NO_2$, alkyl, alkoxy, $C_1$–$C_6$ perfluorinated alkyl, OH or the $C_1$–$C_4$ esters or alkyl ethers thereof, —CN, —O—$R^1$, —O—Ar, —S—$R^1$, —S—Ar, —SO—$R^1$, —SO—Ar, —$SO_2$—$R^1$, —$SO_2$—Ar, —CO—$R^1$, —CO—Ar, —$CO_2$—$R^1$, or —$CO_2$—Ar; and Y is selected from a) the moiety:

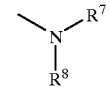

wherein $R_7$ and $R_8$ are independently selected from the group of H, $C_1$–$C_6$ alkyl, or phenyl; or b) an optionally substituted five-, six- or seven-membered saturated, unsaturated or partially unsaturated heterocycle or bicyclic heterocycle containing up to two heteroatoms selected from the group consisting of —O—, —NH—, —N($C_1C_4$ alkyl)—, —N=, and —S(O)$_n$—.

9 Claims, No Drawings

ARYLOXY-ALKYL-DIALKYLAMINES

This application claims the benefit of U.S. Provisional Application No. Ser. 60/090,099, which was converted from U.S. patent application No. 08/950,818, filed Oct. 15, 1997, pursuant to a petition filed under 37 C.F.R. 1.53(c)(2)(i), which is a division under 37 C.F.R. 1.53(b) of prior application Ser. No. 09/161,653, filed Sep. 28, 1998, now pending, which claims the benefit of Provisional Application No. 60/090,099, filed Oct. 15, 1997.

This invention provides novel compounds useful in the production of biologically active compounds, as well as processes for their production. More particularly, the present invention provides novel aryloxyalkyl-dialkylamines which may be used in the production of pharmaceutical products.

BACKGROUND OF THE INVENTION

Matrix metalloproteinases (MMPs) are a group of enzymes that have been implicated in the pathological destruction of connective tissue and basement membranes [Woessner, J. F., Jr. *FASEB J.* 1991, 5, 2145; Birkedal-Hansen, H.; Moore, W. G. I.; Bodden, M. K.; Windsor, L. J.; Birkedal-Hansen, B.; DeCarlo, A.; Engler, J. A. *Crit. Rev. Oral Biol. Med.* 1993, 4, 197; Cawston, T. E. *Pharmacol. Ther.* 1996, 70, 163; Powell, W. C.; Matrisian, L. M. *Cur. Top. Microbiol. and Immunol.* 1996, 213, 1]. These zinc containing endopeptidases consist of several subsets of enzymes including collagenases, stromelysins and gelatinases. Of these classes, the gelatinases have been shown to be the MMPs most intimately involved with the growth and spread of tumors, while the collagenases have been associated with the pathogenesis of osteoarthritis [Howell, D. S.; Pelletier, J. -P. In *Arthritis and Allied Conditions;* McCarthy, D. J.; Koopman, W. J., Eds.; Lea and Febiger: Philadelphia, 1993; 12*th Edition* Vol. 2, pp. 1723; Dean, D. D. *Sem. Arthritis Rheum.* 1991, 20, 2; Crawford, H. C.; Matrisian, L. M. *Invasion Metast.* 1994–95, 14, 234; Ray, J. M.; Stetler-Stevenson, W. G. *Exp. Opin. Invest. Drugs,* 1996, 5, 323].

The use of hormone replacement therapy for bone loss prevention in post-menopausal women is well precedented. The normal protocol calls for estrogen supplementation using such formulations containing estrone, estriol, ethynyl estradiol or conjugated estrogens isolated from natural sources (i.e. Premarin® conjugated estrogens from Wyeth-Ayerst). In some patients, therapy may be contraindicated due to the proliferative effects unopposed estrogens (estrogens not given in combination with progestins) have on uterine tissue. This proliferation is associated with increased risk for endometriosis and/or endometrial cancer. The effects of unopposed estrogens on breast tissue is less clear, but is of some concern. The need for estrogens which can maintain the bone sparing effect while minimizing the proliferative effects in the uterus and breast is evident. Certain nonsteroidal antiestrogens have been shown to maintain bone mass in the ovariectomized rat model as well as in human clinical trials. Tamoxifen (sold as Novadex® brand tamoxifen citrate by Zeneca Pharmaceuticals, Wilmington, Del.), for example, is a useful palliative for the treatment of breast cancer and has been demonstrated to exert an estrogen agonist-like effect on the bone, in humans. However, it is also a partial agonist in the uterus and this is cause for some concern. Raloxifene, a benzthiophene antiestrogen, has been shown to stimulate uterine growth in the ovariectomized rat to a lesser extent than Tamoxifen while maintainig the ability to spare bone. A suitable review of tissue selective estrogens is seen in the article "Tissue-Selective Actions Of Estrogen Analogs", *Bone* Vol. 17, No. 4 October 1995, 181S–190S.

The present invention provides novel intermediates which may be used in the production of pharmaceutical compounds for anti-estrogenic and MMP-inhibiting utilities. The use of 4-carbamoyhmethoxy-methoxy-benzyl chloride compounds of the structures:

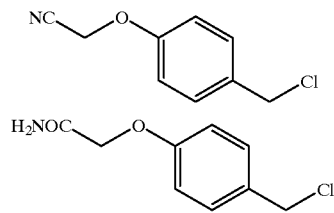

are taught in NL 6402393; 1964; and Chem. Abstr. 1965, 62, 7698.

The use of 4-(2-dialkylamino-ethoxy)benzoyl chloride compounds of the structures:

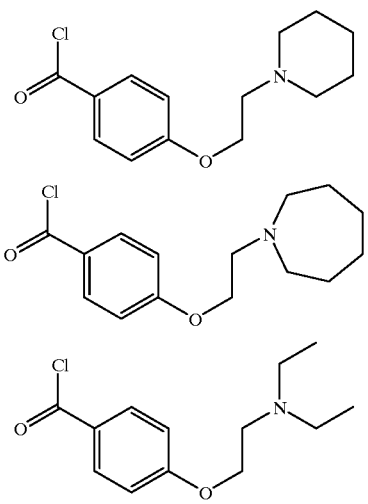

are disclosed in Sharpe, C. J. et. al. J. Med. Chem. 1972, 15, 523 and Jones, C. D. et. al. J. Med. Chem. 1984, 27, 1057. Similarly, the use of 4-(2-quinolinylmethoxy)benzyl chloride

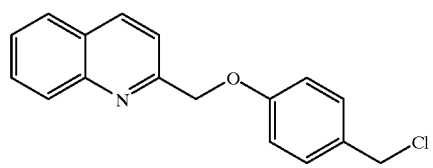

is disclosed by Huang, F -C. et. al. J. Med. Chem. 1990, 33, 1194.

SUMMARY OF THE INVENTION

The present invention provides new compounds, as well as methods for the production thereof, which can be used in the production of pharmaceutically active compounds. The compounds of this invention can particularly be used as intermediates in the production of pharmaceutical compounds, such as low molecular weight, non-peptide inhibitors of matrix metalloproteinases (e.g. gelatinases, stromelysins and collagenases) and TNF-__ converting enzyme (TACE, tumor necrosis factor-__ converting enzyme) which are useful for the treatment of diseases in which these enzymes are implicated such as arthritis, tumor metastasis, tissue ulceration, abnormal wound healing, periodontal disease, bone disease, proteinuria, aneurysmal aortic disease, degenerative cartilage loss following traumatic joint injury, demyelinating diseases of the nervous system and HIV infection. In addition, the compounds of this invention can be used to produce compounds which behave like estrogen agonists by lowering cholesterol and preventing bone loss. Therefore, these compounds are useful for treating many maladies including osteoporosis, prostatic hypertrophy, infertility, breast cancer, endometrial hyperplasia and cancer, cardiovascular disease, contraception, Alzheimer's disease and melanoma.

The present invention includes novel compounds of formula (I):

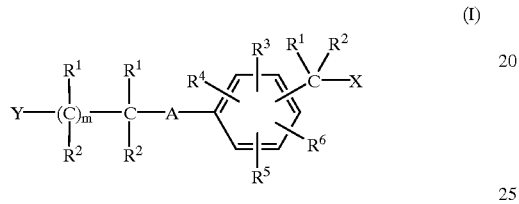

(I)

wherein:
$R^1$ and $R^2$ are, independently, selected from H; $C_1$-$C_{12}$ alkyl, preferably $C_1$-$C_6$ alkyl; or $C_1$-$C_6$ perfluorinated alkyl, preferably —$CF_3$;

X is a leaving group, such as halogen, —O—$SO_2$—$CH_3$, —O—$SO_2$—$CF_3$, or a moiety of the structure:

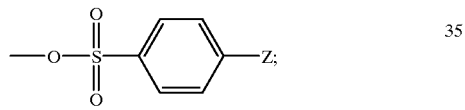

Z is selected from —$NO_2$, halogen, —$CH_3$ or —$CF_3$;
A is selected from —O— or —S—, —SO— or —$SO_2$—;
m is an integer from 0 to 3, preferably 1;
$R^3$, $R^4$, $R^5$, and $R^6$ are independently selected from H, halogen, —$NO_2$, alkyl (preferably $C_1$-$C_{12}$ alkyl, more preferably $C_1$-$C_6$ alkyl), alkoxy (preferably $C_1$-$C_{12}$ alkoxy, more preferably $C_1$-$C_6$ alkoxy), $C_1$-$C_6$ perfluorinated alkyl (preferably —$CF_3$), OH or the $C_1$-$C_4$ esters or alkyl ethers thereof, —CN, —O—$R^1$, —O—Ar, —S—$R^1$, —S—Ar, —SO—$R^1$, —SO—Ar, —$SO_2$—$R^1$, —$SO_2$—Ar, —CO—$R^1$, —CO—Ar, —$CO_2$—$R^1$, or —$CO_2$—Ar;

Y is selected from:
a) the moiety:

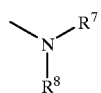

wherein $R_7$ and $R_8$ are independently selected from the group of H, $C_1$-$C_6$ alkyl, or phenyl.
b) a five-membered saturated, unsaturated or partially unsaturated heterocycle containing up to two heteroatoms selected from the group consisting of —O—, —NH—, —N($C_1C_4$ alkyl)—, —N=, and —S(O)$_n$—, wherein n is an integer of from 0–2,
optionally substituted with 1–3 substituents independently selected from the group consisting of hydrogen, hydroxyl, halo, $C_1$-$C_4$ alkyl, trihalomethyl, $C_1$-$C_4$ alkoxy, trihalomethoxy, $C_1$-$C_4$ acyloxy, $C_1$-$C_4$ alkylthio, $C_1$-$C_4$ alkylsulfinyl, $C_1$-$C_4$ alkylsulfonyl, hydroxy ($C_1$-$C_4$)alkyl, phenyl optionally substituted with 1–3 ($C_1$-$C_4$)alkyl, —$CO_2$H, —CN, —$CONHR^1$, —$NH_2$, $C_1$-$C_4$ alkylamino, $C_1$-$C_4$ dialkylamino, —$NHSO_2R^1$, —$NHCOR^1$, —$NO_2$;
c) a six-membered saturated, unsaturated or partially unsaturated heterocycle containing up to two heteroatoms selected from the group consisting of —O—, —NH—, —N($C_1C_4$ alkyl)—, —N=, and —S(O)$_n$—, wherein n is an integer of from 0–2, optionally substituted with 1–3 substituents independently selected from the group consisting of hydrogen, hydroxyl, halo, $C_1$-$C_4$ alkyl, trihalomethyl, $C_1$-$C_4$ alkoxy, trihalomethoxy, $C_1$-$C_4$ acyloxy, $C_1$-$C_4$ alkylthio, $C_1$-$C_4$ alkylsulfinyl, $C_1$-$C_4$ alkylsulfonyl, hydroxy ($C_1$-$C_4$)alkyl, phenyl optionally substituted with 1–3 ($C_1$-$C_4$)alkyl, —$CO_2$H, —CN, —$CONHR^1$, —$NH_2$, $C_1$-$C_4$ alkylamino, $C_1$-$C_4$ dialkylamino, —$NHSO_2R^1$, —$NHCOR^1$, —$NO_2$;
d) a seven-membered saturated, unsaturated or partially unsaturated heterocycle containing up to two heteroatoms selected from the group consisting of —O—, —NH—, —N($C_1C_4$ alkyl)—, —N=, and —S(O)$_n$—, wherein n is an integer of from 0–2,- optionally substituted with 1–3 substituents independently selected from the group consisting of hydrogen, hydroxyl, halo, $C_1$-$C_4$ alkyl, trihalomethyl, $C_1$-$C_4$ alkoxy, trihalomethoxy, $C_1$-$C_4$ acyloxy, $C_1$-$C_4$ alkylthio, $C_1$-$C_4$ alkylsulfinyl, $C_1$-$C_4$ alkylsulfonyl, hydroxy ($C_1$-$C_4$)alkyl, phenyl optionally substituted with 1–3 ($C_1$-$C_4$)alkyl, —$CO_2$H, —CN, —$CONHR^1$, —$NH_2$, $C_1$-$C_4$ alkylamino, $C_1$-$C_4$ dialkylamino, —$NOHSO_2R^1$, —$NHCOR^1$, —$NO_2$; or
e) a bicyclic heterocycle containing from 6–12 carbon atoms either bridged or fused and containing up to two heteroatoms selected from the group consisting of —O—, —NH—, —N($C_1C_4$ alkyl)—, and —S(O)$_n$—, wherein n is an integer of from 0–2, optionally substituted with 1–3 substituents independently selected from the group consisting of hydrogen, hydroxyl, halo, $C_1$-$C_4$ alkyl, trihalomethyl, $C_1$-$C_4$ alkoxy, trihalomethoxy, $C_1$-$C_4$ acyloxy, $C_1$-$C_4$ alkylthio, $C_1$-$C_4$ alkylsulfinyl, $C_1$-$C_4$ alkylsulfonyl, hydroxy ($C_{1-4}$)alkyl, phenyl optionally substituted with 1–3 ($C_1$-$C_4$)alkyl, —$CO_2$H, —CN, —$CONHR^1$, —$NH_2$, $C_1$-$C_4$ alkylamino, $C_1$-$C_4$ dialkylamino, —$NHSO_2R^1$, —$NHCOR^1$, —$NO_2$; and the pharmaceutically acceptable salts thereof.

It is understood in the generic description above and the other groups herein that, in each instance they may appear, $R^1$ and $R^2$ are independently selected from the group of substituents listed. Any $R^1$ listed in any structure herein need not represent the same substituent as another $R^1$, nor does any $R^2$ have to be the same substituent as any other $R^2$, even if more than one $R^1$ or $R^2$ are found in the same structure.

In the description above, the symbol "Ar" indicates an monocyclic or polycyclic aryl or heteroaryl groups which may be optionally substituted by one or more substituents selected from halogen, $C_{1-6}$ alkyl or —$CF_3$. Examples of preferred aryl groups include anthracenyl, and phenanthrenyl groups, as well as the more preferred phenyl, cumenyl, mesityl, tolyl, xylyl, and naphthalenyl groups. Examples of preferred heteroaryl groups include indolizinyl, indazolyl, indazolyl, purinyl, quinozinyl, isoquinolinyl, quinolinyl, phthalozinyl, napthyridinyl, quinoxalinyl, quinazolinyl, cinnolinyl, and pteridinyl groups, and the like, as well as the more preferred pyridyl, pyrazinyl, pyriridinyl, pyridizinyl and indolyl groups.

The invention includes acceptable salt forms formed from the addition reaction with either inorganic or organic acids. Inorganic acids such as hydrochloric acid, hydrobromic acid, hydroiodic acid, sufuric acid, phoshoric acid, nitric acid useful as well as organic acids such as acetic acid, propionic acid, citric acid, maleic acid, malic acid, tartaric acid, phthalic acid, succinic acid, methanesulfonic acid, toluenesulfonic acid, napthalenesulfonic acid, camphorsulfonic acid, benzenesulfonic acid are useful. It is known that compounds possessing a basic nitrogen can be complexed with many different acids (both protic and not protic) and usually it is preferred to administer a compound of this invention in the form of an acid addition salt. Additionally, this invention includes quaternary ammonium salts of the compounds herein, which can be prepared by reacting the nucleophilic amines of the side chain with a suitably reactive alkylating agent such as alkyl halide or benzyl halide.

Among the preferred compounds of this invention are those of the formula (I):

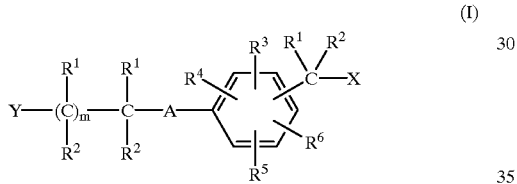

(I)

wherein:
R$^1$ and R$^2$ are, independently, selected from H; C$_1$–C$_{12}$ alkyl, preferably C$_1$–C$_6$ alkyl; or C$_1$–$_6$ perfluorinated alkyl, preferably —CF$_3$;
X is a leaving group, such as halogen, —O—SO$_2$—CH$_3$, —O—SO$_2$—CF$_3$, or a moiety of the structure:

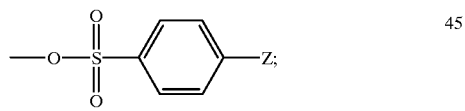

Z is selected from —NO$_2$, halogen, —CH$_3$ or —CF$_3$;
A is selected from —O— or —S—, —SO— or —SO$_2$—;
m is an integer from 0 to 3, preferably 1;
Y is selected from:
a) the moiety:

wherein R$_7$ and R$_8$ are independently selected from the group of H, C$_1$–C$_6$ alkyl, or phenyl.
b) a group selected from thiophene, furan, pyrrole, imidazole, pyrazole, thiazole, isothiazole, isoxazole, or oxathiolane, the group being optionally substituted with 1–3 substituents independently selected from the group consisting of hydrogen, hydroxyl, halo, C$_1$–C$_4$ alkyl, trihalomethyl, C$_1$–C$_4$ alkoxy, trihalomethoxy, C$_1$–C$_4$ acyloxy, C$_1$–C$_4$ alkylthio, C$_1$–C$_4$ alkylsulfinyl, C$_1$–C$_4$ alkylsulfonyl, hydroxy (C$_1$–C$_4$)alkyl, phenyl optionally substituted with 1–3 (C$_1$–C$_4$)alky, —CO$_2$H, —CN, —CONHR$^1$, —NH$_2$, C$_1$–C$_4$ alkylamino, C$_1$–C$_4$ dialkylamino, —NHSO$_2$R$^1$, —NHCOR$^1$, —NO$_2$;
c) a group selected from pyridine, pyrazine, pyrirnidine, pyridazine, piperidine, morphonine and pyran, the group being optionally substituted with 1–3 substituents independently selected from the group consisting of hydrogen, hydroxyl, halo, C$_1$–C$_4$ alkyl, trihalomethyl, C$_1$–C$_4$ alkoxy, trihalomethoxy, C$_1$–C$_4$ acyloxy, C$_1$–C$_4$ alkylthio, C$_1$–C$_4$ alkylsulfinyl, C$_1$–C$_4$ alkylsulfonyl, hydroxy (C$_1$–C$_4$) alkyl, phenyl optionally substituted with 1–3 (C$_1$–C$_4$)alkyl, —CO$_2$H, —CN, —CONHR$^1$, —NH$_2$, C$_1$–C$_4$ alkylamino, C$_1$–C$_4$ dialkylamino, —NHSO$_2$R$^1$, —NHCOR$^1$, —NO$_2$;
d) a group selected from azepine, diazepine, oxazepine, thiazepine, oxapin and thiepin, the group being optionally substituted with 1–3 substituents independently selected from the group consisting of hydrogen, hydroxyl, halo, C$_1$–C$_4$ alkyl, trihalomethyl, C$_1$–C$_4$ alkoxy, trihalomethoxy, C$_1$–C$_4$ acyloxy, C$_1$–C$_4$ alkylthio, C$_1$–C$_4$ alkylsulfonyl, C$_1$–C$_4$ alkylsulfonyl, hydroxy (C$_1$–C$_4$)alkyl, phenyl optionally substituted with 1–3 (C$_1$–C$_4$)alkyl, —CO$_2$H, —CN, —CONHR$^1$, —NH$_2$, C$_1$–C$_4$ alkylamino, C$_1$–C$_4$ dialkylamino, —NHSO$_2$R$^1$, —NHCOR$^1$, —NO$_2$; or
e) a bicyclic heterocycle selected from the group of benzofuran, isobenzofuran, benzothiophene, indole, isoindole, indolizine, indazole, purine, quinolizine, isoquinoline, quinoline, phthalazine, napthryidine, quinoxaline, quinazoline, and cinnoline, the group being optionally substituted with 1–3 substituents independently selected from the group consisting of hydrogen, hydroxyl, halo, C$_1$–C$_4$ alkyl, trihalomethyl, C$_1$–C$_4$ alkoxy, trihalomethoxy, C$_1$–C$_4$ acyloxy, C$_1$–C$_4$ alkylthio, C$_1$–C$_4$ alkylsulfinyl, C$_1$–C$_4$ alkylsulfonyl, hydroxy (C$_1$–C$_4$)alkyl, phenyl optionally substituted with 1–3 (C$_1$–C$_4$)alkyl, —CO$_2$H, —CN, —CONHR$^1$, —NH$_2$, C$_1$–C$_4$ alkylamino, C$_1$–C$_4$ dialkylamino, —NHSO$_2$R$^1$, —NHCOR$^1$, —NO$_2$; and the pharmaceutically acceptable salts thereof.

Further preferred compounds of this invention are those of the formula (I):

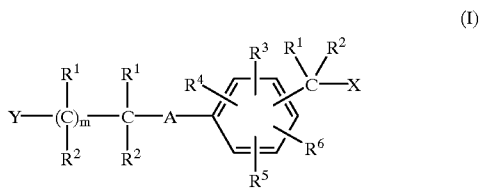

(I)

wherein:
R$^1$ and R$^2$ are, independently, selected from H; C$_1$–C$_{12}$ alkyl, preferably C$_1$–C$_6$ alkyl; or C$_1$–C$_6$ perfluorinated alkyl, preferably —CF$_3$;
X is a leaving group, such as halogen, —O—SO$_2$—CH$_3$, —O—SO$_2$—CF$_3$, or a moiety of the structure:

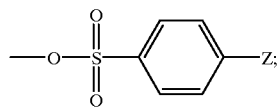

Z is selected from —NO$_2$, halogen, —CH$_3$ or —CF$_3$;
A is selected from —O— or —S—, —SO— or —SO$_2$—;
m is an integer from 0 to 3, preferably 1;
Y is selected from:
  a) the moiety:

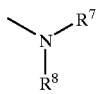

wherein R$_7$ and R$_8$ are independently selected from the group of H, C$_1$–C$_6$ alkyl, orphenyl; or
  b) a group selected from thiophene, furan, pyrrole, imidazole, pyrazole, thiazole, pyridine, pyrazine, pyrimidine, pyridazine, piperidine, indole or benzofuran, the group being optionally substituted with 1–3 substituents independently selected from the group consisting of hydrogen, hydroxyl, halo, C$_1$–C$_4$ alkyl, trihalomethyl, C$_1$–C$_4$ alkoxy, trihalomethoxy, C$_1$–C$_4$ acyloxy, C$_1$–C$_4$ alkylthio, C$_1$–C$_4$ alkylsulfinyl, C$_1$–C$_4$ alkylsulfonyl, hydroxy (C$_1$–C$_4$)alkyl, phenyl optionally substituted with 1–3 (C$_1$–C$_4$)alkyl, —CO$_2$H, —CN, —CONHR$^1$, —NH$_2$, C$_1$–C$_4$ alkylamino, C$_1$–C$_4$ dialkylamino, —NHSO$_2$R$^1$, —NHCOR$^1$, —NO$_2$; and the pharmaceutically acceptable salts thereof.

Among the more preferred compounds of the present invention are those having the general formula (II)

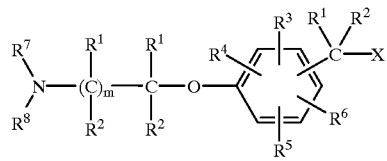

wherein:
  R$^1$ and R$^2$ are, independently, selected from H, C$_1$–C$_6$ alkyl or C$_1$–C$_6$ perfluorinated alkyl, preferably, among the perfluorinated alkyl groups, —CF$_3$;
  R$^3$, R$^4$, R$^5$, and R$^6$ are independently selected from H, OH or the C$_1$–C$_4$ esters or alkyl ethers thereof, halogen, —CN, C$_1$–C$_6$ alkyl, or trifluoromethyl,
  m is an integer from 0 to 3, preferably 1;
  R$^7$ and R$^8$ are selected independently from H, C$_1$–C$_6$ alkyl, or combined by —(CH$_2$)p—, wherein p is an integer of from 2 to 6, so as to form a ring, the ring being optionally substituted by up to three substituents selected from the group of hydrogen, hydroxyl, halo, C$_1$–C$_4$ alkyl, trihalomethyl, C$_1$–C$_4$ alkoxy, trihalomethoxy, C$_1$–C$_4$ alkylthio, C$_1$–C$_4$ alkylsulfinyl, C$_1$–C$_4$ alkylsulfonyl, hydroxy (C$_1$–C$_4$)alkyl, —CO$_2$H, —CN, —CONH(C$_1$–C$_4$), —NH$_2$, C$_1$–C$_4$ alkylamino, C$_1$–C$_4$ dialkylamino, —NHSO$_2$(C$_1$–C$_4$), —NHCO (C$_1$–C$_4$), and —NO$_3$; and
  X is as defined above;
and the pharmaceutically acceptable salts thereof.

Also among the more preferred compounds of the present invention are those having the general formula (III)

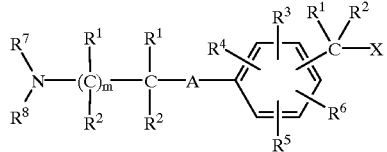

wherein:
  R$^1$ and R$^2$ are, independently, selected from H, C$_1$–C$_6$ alkyl or C$_1$–C$_6$ perfluorinated alkyl, preferably, among the perfluorinated alkyl groups, —CF$_3$;
  R$^3$, R$^4$, R$^5$, and R$^6$ are independently selected from H, OH or the C$_1$–C$_4$ esters or alkyl ethers thereof, halogen, —CN, C$_1$–C$_6$ alkyl, or trifluoromethyl,
  m is an integer from 0 to 3, preferably 1;
  A is selected from —S—, —SO— or —SO$_2$—;
  R$^7$ and R$^8$ are selected independently from H, C$_1$–C$_6$ alkyl, or combined by —(CH$_2$)p—, wherein p is an integer of from 2 to 6, so as to form a ring, the ring being optionally substituted by up to three substituents selected from the group of hydrogen, hydroxyl, halo, C$_1$–C$_4$ alkyl, trihalomethyl, C$_1$–C$_4$ alkoxy, trihalomethoxy, C$_1$–C$_4$ alkylthio, C$_1$–C$_4$ alkylsulfinyl, C$_1$–C$_4$ alkylsulfonyl, hydroxy (C$_1$–C$_4$)alkyl, —CO$_2$H, —CN, —CONH(C$_1$–C$_4$), —NH$_3$, C$_1$–C$_4$ alkylamino, C$_1$–C$_4$ dialkylamino, —NHSO$_2$(C$_1$–C$_4$), —NHCO (C$_1$–C$_4$), and —NO$_2$; and
  X is as defined above;
and the pharmaceutically acceptable salts thereof.

Among the most preferred compounds of the present invention are those having the structural formulas II or III, above, wherein R$^3$–R$^6$ are as defined above; X is selected from the group of Cl, —CF$_3$, or —CH$_3$; and Y is the moiety

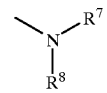

and R$^7$ and R$^8$ are concatenated together as —(CH$_2$)$_r$—, wherein r is an integer of from 4 to 6, to form a ring optionally substituted by up to three subsituents selected from the group of hydrogen, hydroxyl, halo, C$_1$–C$_4$ alkyl, trihalomethyl, C$_1$–C$_4$ alkoxy, trihalomethoxy, C$_1$–C$_4$ alkylthio, C$_1$–C$_4$ alkylsulfinyl, C$_1$–C$_4$ alkylsulfonyl, hydroxy (C$_1$–C$_4$)alkyl, —CO$_2$H, —CN, —CONH(C$_1$–C$_4$), —NH$_3$, C$_1$–C$_4$ alkylamino, C$_1$–C$_4$ dialkylamino, —NHSO$_2$ (C$_1$–C$_4$), —NHCO(C$_1$–C$_4$), and —NO$_2$; and the pharmaceutically acceptable salts thereof.

It is further preferred that, when R$^7$ and R$^8$ are concatenated together as —(CH$_2$)p— or —(CH$_2$)$_r$—, the ring so formed is optionally substituted with 1–3 substituents selected from a group containing C$_1$–C$_3$ alkyl, trifluoromethyl, halogen, hydrogen, phenyl, nitro, —CN.

This invention also includes a process for making the compounds above. Compounds of this invention in which "A" is oxygen can be synthesized by the process steps of:- a) alkylating a relevant hydroxybenzaldehyde of the formula:

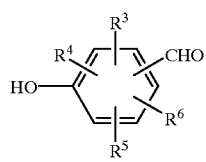

wherein $R^3$–$R^6$ are as defined above, with a relevant alkyl halide of the formula:

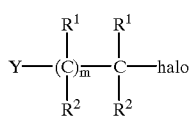

wherein Y, $R^1$, $R^2$ and m are as defined in the generic and subgeneric groups above and halo can be Cl, F, Br or I, to produce an aldehyde of the formula:

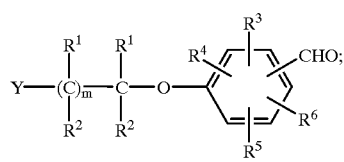

b) reducing the aldehyde product of step a), to yield the relevant alcohol having a formula:

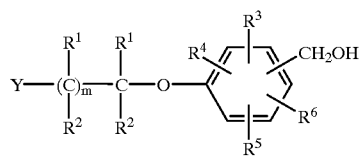

c) converting the alcohol of step b) to its hydrochloride salt, such as with HCl/THF and d) converting the alcohol to a preferred leaving group, such as through treatment with methanesulfonyl chloride, toluenesulfonyl chloride, or trifluoroacetic anhydride in the presence of a base like pyridine or triethylamine.

Similarly, the present invention provides a process for producing compounds of this invention wherein "A" is sulfur through the steps of:

a) alkylating a compound of the formula

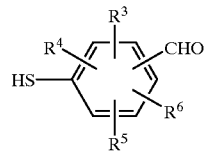

with an alkylating agent of the formula:

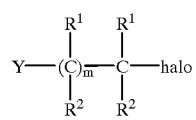

wherein Y and m are as defined above and halo is selected from Cl, F, Br or I, to produce an aldehyde of the formula:

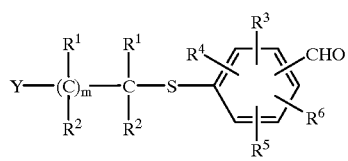

b) reduction of the aldehyde product of step a), such as with sodium borohydride, to an alcohol of the formula;

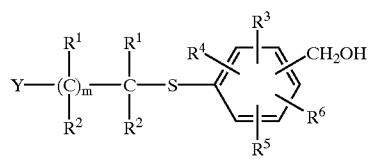

c) treatment of the alcohol of step b) with gaseous HCl to generate its hydrochloride; and d) converting the alcohol hydrochloride product of step c) to a preferred leaving group, such as through treatment with methanesulfonyl chloride, toluenesulfonyl chloride, or trifluoroacetic anhydride in the presence of a base like pyridine or triethylamine or continued treatment with HCl to form the corresponding benzyl chloride; and, e) optionally, completing controlled oxidation of the sulfur to sulfoxide or to sulfone, such as with m-chloroperbenzoic acid.

The starting thiophenoxide aldehyde material of step a), above, may be generated from its corresponding thiophenol aldehyde, such as with sodium hydride, which may or may not be considered a step of the process, above.

DETAILED DESCRIPTION OF THE INVENTION

The following reactions Schemes I through IV demonstrate the synthesis of compounds of the present invention, utilizing different variables for "Y". The reagents and solvents for the individual steps are given for illustrative purposes only and may be replaced by other reagents and solvents known to those skilled in the art.

Scheme I
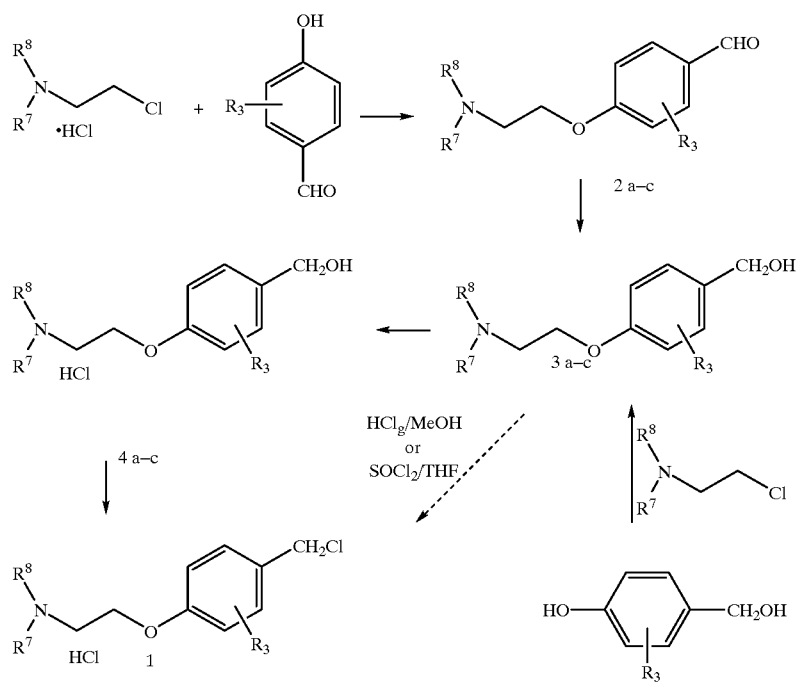
a, R7R8 = (CH2)5; b, R7R8 = (CH2)6; c, R7 = R8 = CH3 and R3 = H.
a, R7B8=(CH2)5; b, R7R8=(CH2)6; c, R7=R8=CH3 and R3=H
Scheme II
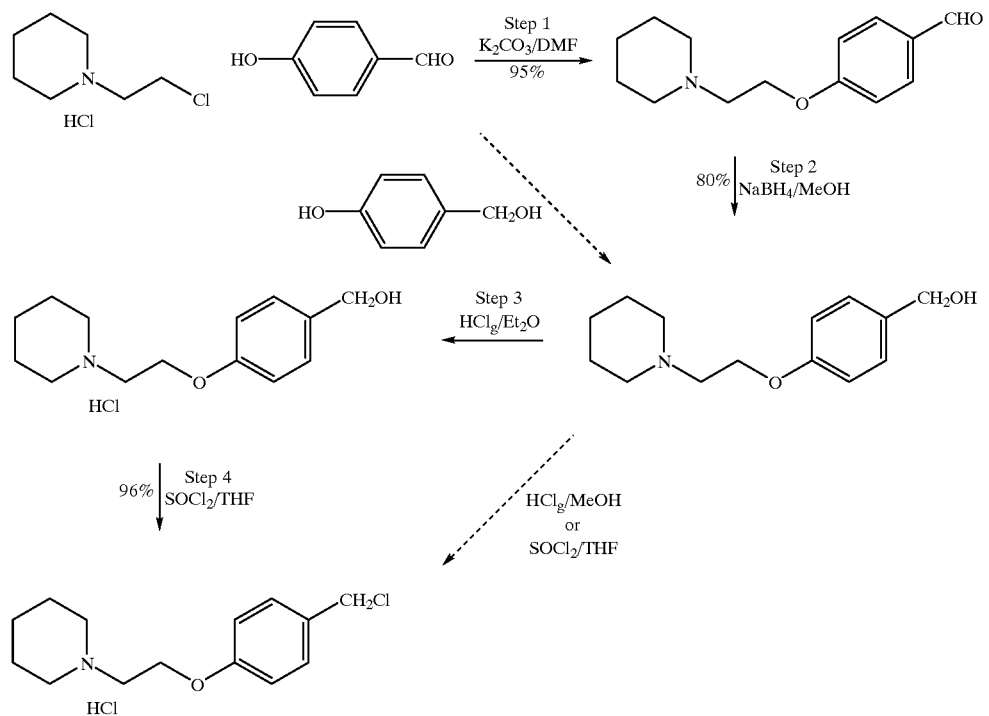

Scheme IIa

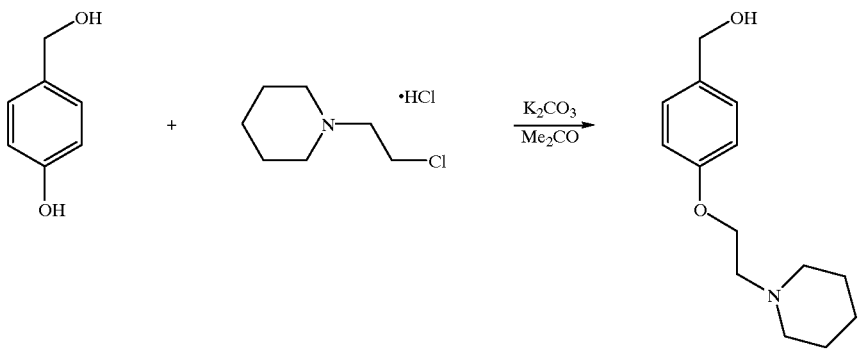

Scheme IIa offers an alternative synthesis of the benzyl alcohols of this invention, exemplifying the synthesis of 4-(2-piperidinylethoxy)benzyl alcohol. In this synthesis 4hydroxybenzyl alcohol is treated with a desired aryl amino alkyl chloride to afford the corresponding alkoxy benzyl alcohol. In the specific example of Scheme IIa, 4-hydroxybenzyl alcohol can be treated with 1-(2-chloroethyl)-piperidine hydrochloride in the presence of $K_2CO_3/Me_2CO$ to yield 4(2-piperidinylethoxy)benzyl alcohol.

Scheme IIa also more specifically illustrates another preferred embodiment of the present invention. This invention also includes a process for producing useful alcohol compounds of the formula:

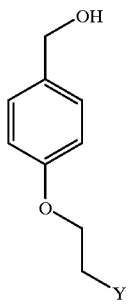

wherein Y represents the Y groups and their optional substituents as described most generically above.

In a preferred subgroup of this process, Y represents:

a) the moiety

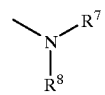

wherein $R_7$ and $R_8$ are independently selected from the group of H, $C_1$–$C_6$ alkyl, or phenyl; or b) a five-, six- or seven-membered unsaturated or partially unsaturated heterocyclic ring containing one or two nitrogen atoms, the heterocyclic ring being bound to the ethoxy bridge at a nitrogen atom in the ring and being optionally substituted by from 1 to 3 groups selected from halogen, $C_1$–$C_6$ alkyl, $C_1$–$C_6$ alkoxy, $C_1$–$C_6$ thioalkyl, —$CF_3$, or —$NO_2$.

Among the preferred Y groups of this process are azepine, pyrrole, imidazoline, imidazolidine, hexamethyleneimine, pyrrolidine, pyrazolidine, pyrazoline, piperidine, piperazine, The process comprises reacting, in an alkaline medium, 4hydroxybenzyl alcohol with a salt, such as an acetate, hydrochloride, hydrobromide or hydroiodide salt, of a compound of the formula:

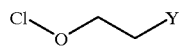

wherein Y is as defined above.

This reaction is carried out in an organic solvent or solvent system, such as in acetone, dimethylformamide or tetrahydrofuran. Preferably the pH of the medium is maintained above a pH of 8, more preferably above a pH of 9.

Scheme III

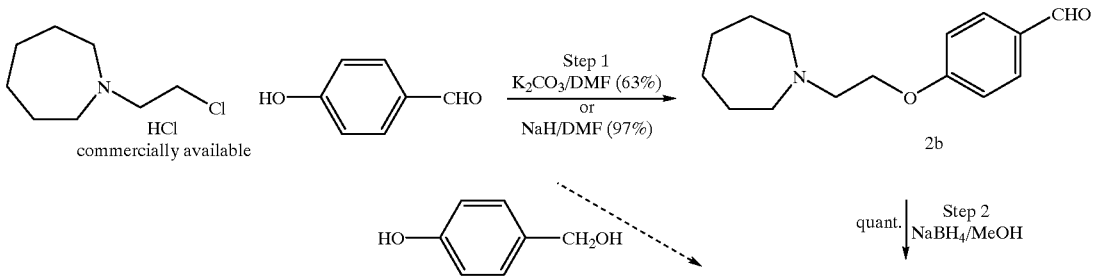

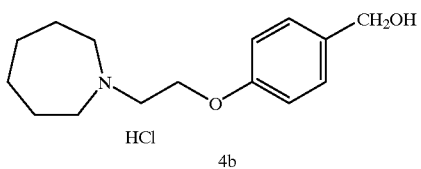

4b

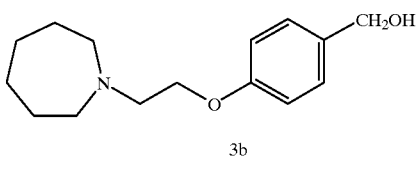

3b

-continued

Step 3
HCl$_g$/THF

Step 4
67% SOCl$_2$/THF

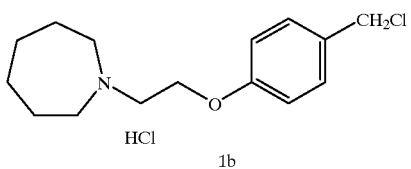

1b

HCl$_g$/MeOH
or
SOCl$_2$/THF

Scheme IV

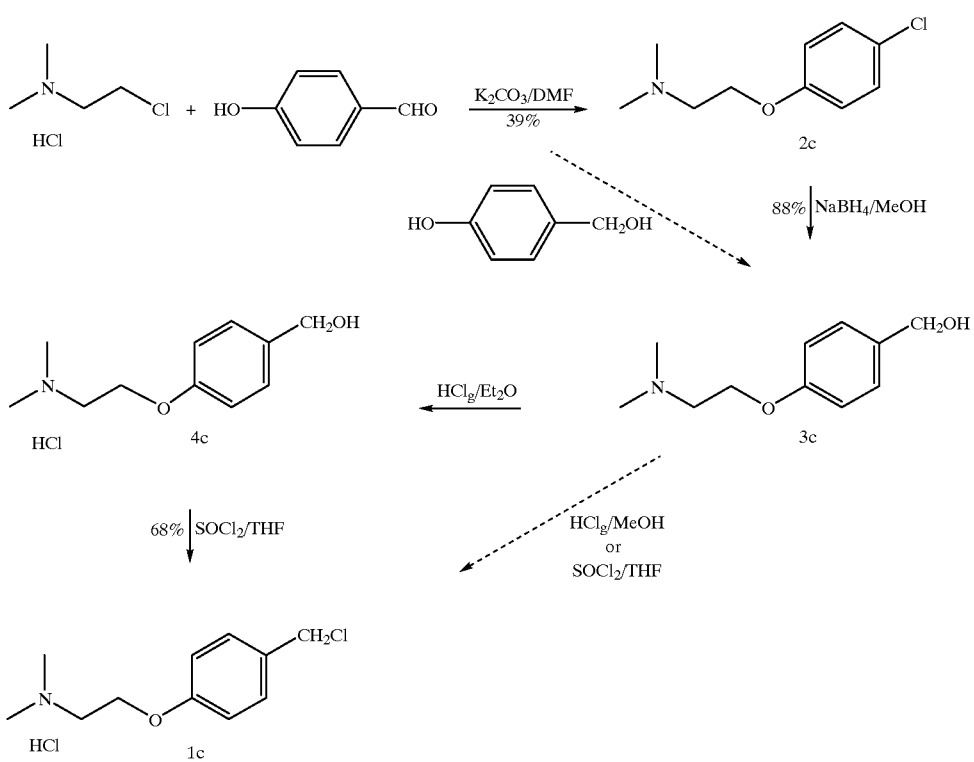

Utilizing similar steps, compounds of this invention wherein "A" is sulfur may be produced as shown in Scheme V, below. In a first step thiophenoxide may be produced with sodium hydride, followed by alkylation and reduction to the relevant aldehyde, such as with sodium borohydride or catalytically with Hydrogen and Raney Nickel or platinum or palladium on carbon catalysts. The resulting alcohol may then be treated with gaseous HCl to generate its hydrochloride, with continued HCl treatment to form a benzyl chloride. The final product may then be formed by controlled oxidation of the sulfur to sulfoxide, and then to sulfone, such as with m-chloroperbenzoic acid.

Scheme V

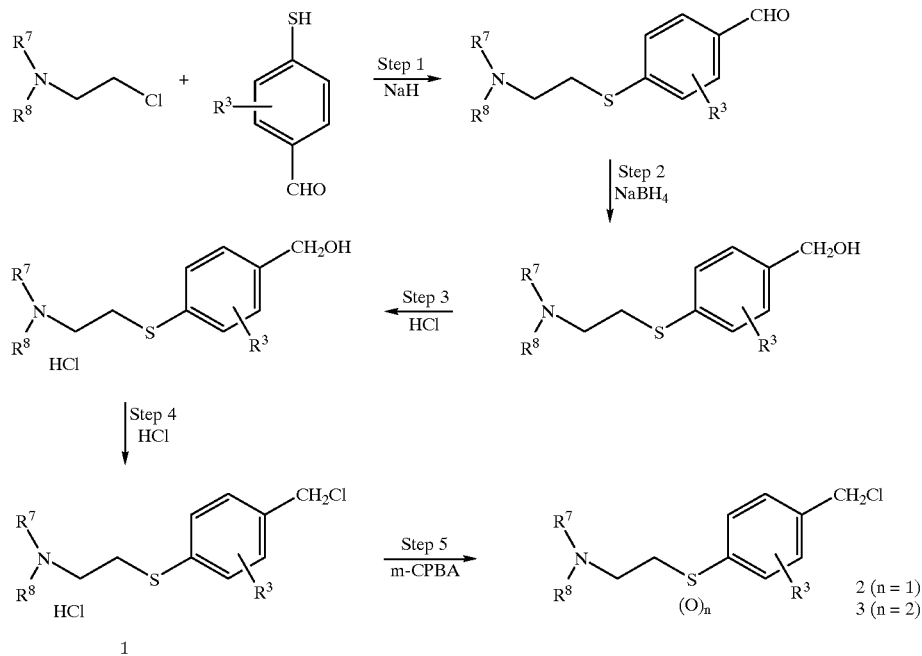

The following examples are presented to illustrate rather than limit the scope of the invention.

EXAMPLE 1

4-(2-piperidine-1-yl-ethoxy)-benzyl aldehyde (2a)

To a well-stirred slurry of p-hydroxybenzaldehyde (83.5 g, 0.68 mol, 1.05 eq.) and $K_2CO_3$ (224 g, 1.6 mol, 2.5 eq.) in DMF (1 L), 1-(2-chloroethyl)piperidine hydrochloride (120 g, 0.65 mol, 1.0 eq.) is added. The reaction mixture is refluxed for 2 h with vigorous mechanical stirring. TLC at this point shows no starting material, mostly product (EtOAc/hexane 1:1). The reaction mixture is filtered through Celite, deluted with EtOAc (2 L), and washed with water (3×500 mL). The organic layer is concentrated on a rotary evaporator to give 147 g (97%) of aldehyde (2a) as a yellow oil.

$^1$H NMR ($CDCl_3$/TMS): 9.87 (s, 1H), 7.81 (d, 2H, J 8.7 Hz), 7.01 (d, 2H, J=8.7 Hz), 4.18 (t, 2H, J=6.03 Hz), 2.79 (t, 2H, J=6.03 Hz), 2.51 (m, 4H), 1.6–1.4 (m, 6H)

EXAMPLE 2

4-(2-hexamethyleneimine-1-yl-ethoxy)-benzyl aldehyde (2b)

To a well-stirred slurry of NaH (65 g, 60% oil dispersion, 1.6 mol, 2.2 eq.) in DMF (500 mL) a solution of p-hydroxybenzaldehyde hydrochloride (90 g, 0.74 mol, 1.0 eq.) is added dropwise at 0° C. The reaction mixture is stirred for 30 min, then 4-[2-(hexamethyleneimine)]ethylchloride (153 g, 0.77 mol, 1.0 eq.) is added in portions. The reaction mixture is stirred for 1 h. TLC at this point shows little starting material, mostly product (EtOAc/hexane 1:1). The reaction mixture is diluted with water (1 L), and extracted with ether (5 L). The organic layer is dried over $MgSO_4$, and concentrated on a rotary evaporator to give 176.8 g (97%) of aldehyde (2b) as a yellow oil.

$^1$H NMR ($CDCl_3$/TMS): 9.87 (s, 1H), 7.81 (d, 2H, J=8.7 Hz), 7.02 (d, 2H, J=8.7 Hz), 4.14 (t, 2H, J=6.09 Hz), 2.98 (t, 2H, J=6.14 Hz), 2.78 (m, 4H), 1.66–1.61 (m, 8H)

EXAMPLE 3

4-(2-dimethylamino-ethoxy)-benzyl aldehyde (2c)

To a well-stirred slurry of p-hydroxybenzaldehyde (9.54 g, 0.078 mol, 1.00 eq.) and $K_2CO_3$ (27 g, 0.195 mol, 2.5 eq.) in DMF (100 m L), 1-(2-chloroethyl)dimethylamnine hydrochloride (11.26 g, 0.078 mol, 1.0 eq.) is added. The reaction mixture is stirred for 2 h at 60–70° C. TLC at this point shows no starting material, mostly product (EtOAc/hexane/ EtN 3:7:1). The reaction mixture is poured into water/ice mixture (200 mL), and extracted with $Et_2O$ (3×200 mL). The organic layer is dried with $MgSO_4$, and concentrated on a rotary evaporator to give 5.9 g (39%) of aldehyde (2c) as a pinkish liquid.

$^1$H NMR ($CDCl_3$/TMS): 9.88 (s, 1H), 7.8 (d, 2H, J=8.7 Hz), 7.02 (d, 2H, J=8.7 Hz), 4.15 (t, 2H, J=5.64 Hz), 2.77 (t, 2H, J=5.64 Hz), 2.35 (s, 6H).

EXAMPLE 4

4-(2-piperidine-1-yl-ethoxy)-benzyl alcohol (3a)

To a stirred solution of the aldehyde 2a (115 g, 0.494 mol, 1.0 eq.) in methanol (360 mL) at 0/+5° C. sodium borohydride (9.44 g, 0.249 mol, 0.5 eq.) is added in portions. The reaction is stirred for 30 min. TLC at this point shows no starting material, mostly product (EtOAc/hexane/ triethylamine 3:7:1). The reaction mixture is poured in water (1.1 L), extracted with methylene chloride (3×550 mL), and dried over $MgSO_4$. The solution is concentrated on a rotary evaporator to give 91.6 g (80%) of the alcohol 3a as a thick oil which crystallized instantly on seeding.

$^1$H NMR ($CDCl_3$/TMS): 7.23 (d, 2H, J=8.5 Hz), 6.80 (d, 2H, J=8.5 Hz), 4.56 (s, 2H) 3.99 (t, 2H, J=6.12 Hz), 2.69 (t, 2H, J=6.14 Hz), 2.47 (m, 4H), 1.6–1.25 (m, 6H)

$^{13}$C NMR (DMSO-d$_6$): 158.23, 135.34, 128.70, 114.84, 66.42, 63.44, 58.27, 55.29, 26.45, 24.80

EXAMPLE 5

4-(2-piperidine-1-yl-ethoxy)-benzyl alcohol (3a)

4-hydroxybenzyl alcohol (6.2 g, 0.0.05 mol) was dissolved in aqueus sodium hydroxide (5N, 30 mL). Toluene (30 mL) was added followed by 1-(2-chloroethyl)piperidine hydrochloride (9.29 g, 0.05 mol) and benzyltriethylamumonium bromide (0.3 g). The reaction mixture was heated with vigorous stirring for 1.5 h. The layers were separated, the aqueous layer was extracted with toluene (2×15 mL). Combined organic extracts and organic layer was washed with water (50 mL), brine (50 mL), dried over sodium sulfate, and concentrated on a rotary evaporator to give 8.725 g (75%) of alcohol (3a) as a yellowish brown oil.

EXAMPLE 6

4-(2-hexamethyleneimine -1-yl-ethoxy)-benzyl alcohol (3b)

To a stirred solution of the aldehyde 2b (200 g, 0.72 mol, 1.0 eq.) in methanol (400 mL) at 0/+5° C. sodium borohydride (15.6 g, 0.41 mol, 0.57 eq.) is added in portions. The reaction is stirred for 30 min. TLC at this point shows no starting material, mostly product (EtOAc/hexane/triethylamine 3:7:1). The reaction mixture is diluted with water (400 mL), extracted with methylene chloride (3×400 mL), and dried over MgSO$_4$. The solution is concentrated on a rotary evaporator to give 201 g (100%) of the alcohol 3b as a thick oil.
$^1$H NMR (CDCl$_3$/TMS): 7.27 (d, 2H, J=8.5 Hz), 6.87 (d, 2H, J=8.5 Hz), 4.60 (s, 2H), 4.05 (t, 2H, J=6.21 Hz), 2.93 (t, 2H, J=6.15 Hz), 2.77 (m, 4H), 1.7–1.5 (m, 8H)

EXAMPLE 7

4-(2-dimethylamino-ethoxy)-benzyl alcohol (3c)

To a stirred solution of the aldehyde 2c (5.9 g, 0.031 mol, 1.0 eq.) in methanol (20 mL) at 22° C. sodium borohydride (0.58 g, 0.015 mol, 0.5 eq.) is added in portions. The reaction is stirred for 30 thin. TLC at this point shows no starting material, mostly product (EtOAc/hexane/triethylamine 5:5:1). The reaction mixture is diluted with water (50 mL), extracted with methylene chloride (3×40 mL), and dried over MgSO$_4$. The solution is concentrated on a rotary evaporator to give 5.25 g (88%) of the alcohol 3c as a thick oil.
$^1$H NMR (CDCl$_3$/TMS): 7.25 (d, 2H, J=8.64 Hz), 6.85 (d, 2H, J=8.64 Hz), 4.52 (s, 2H), 3.99 (t, 2H, J=5.88 Hz), 2.67 (t, 2H, J=5.79 Hz), 2.29 (s, 6H)

EXAMPLE 8

(4-Chloromethyl-phenoxy)-ethyl-piperidin-1-yl hydrochloride (1a)

A solution of the alcohol 3a (61.3 g, 0.26 mol, 1 eq.) in THF (500 mL) is cooled to 0/−5° C. (ice-water bath) and bubbled with gaseous HCl. Bubbling is continued until no more thickening of the reaction mixture occurred. The cooling bath is removed. Thionyl chloride (29 mL, 0.39 mol, 1.5 eq.) is added to the thick slurry of hydrochloride 4, and the mixture is heated to 50° C. until clear. The reaction mixture is cooled to −3° C. and stirred for 30 min. The white solid obtained is filtered and dried to give 72 g (96%) of chloride 1a.

4a: $^1$H NMR (DMSO-d$_6$): 10.9 (s, HCl), 7.25 (d, 2H, J=8.5 Hz), 6.94 (d, 2H, J=8.5 Hz), 4.42 (m, 4H), 3.41 (m, 4H)
1a: $^1$H NMR (DMSO-d$_6$): 11 (br s, HCl), 7.39 (d, 2H, J=8.5 Hz), 6.99 (d, 2H, J=8.5 Hz), 4.74 (s, 2H), 4.46 (m, 2H), 3.45 (m, 4H), 2.69 (m, 2H) and 1.9–1.2 (m, 6H)

EXAMPLE 9

(4-Chloromethyl-phenoxy)-ethyl-hexamethyleneimine-1-yl hydrochloride (1b)

To a solution of the alcohol 3b (179 g, 0.72 mol, 1 eq.) in THF (300 mL) a solution of HCl (26.3 g of HCl in 263 mL of THF, 0.72 mol, 1.0 eq.) is added dropwise at 0/+10° C. A white precipitate is formed. Thionyl chloride (80 mL, 1.1 mol, 1.5 eq.) is added to the thick slurry of hydrochloride 4b, and the mixture is heated to 50° C. until clear. The reaction mixture is concentrated to 350 mL, and kept in refrigerator overnight. The white solid obtained is filtered, washed with cold THF (100 mL), and dried to give 147 g (67%) of chloride 1 b.
$^1$H NMR (DMSO-d$_6$): 11 (br s, HCl), 7.40 (d, 2H, J=8.6 Hz), 7.00 (d, 2H, J=8.6 Hz), 4.74 (s; 2H), 4.44 (t, 2H, J=5.25), 3.64–3.39 (m, 4H), 3.25–3.17 (m, 2H 1.84–1.54 (m, 8H)

EXAMPLE 10

(4-Chloromethyl-phenoxy)-ethyl-dimethylamino hydrochloride (1c)

To a solution of the alcohol 3c (5.25 g, 0.027 mol, 1 eq.) in THF (100 mL) gaseous HCl was bubbled at 0/+25° C. for 15 min. A white precipitate is formed. Thionyl chloride (6 mL, 9,6 g, 0.081 mol, 3.0 eq.) is added to the thick slurry of hydrochloride, and the mixture is heated to 30° C. until clear. The reaction mixture is concentrated to 350 mL, and kept in refrigerator overnight. The white solid obtained is filtered, washed with cold THF (100 mL), and dried to give 4.57 g (68%) of chloride 1c.

Among the pharmacologically active compounds which may be produced using the compounds of the present invention are 2-Phenyl-1-[4-(2-aminoethoxy)-benzyl]-indole compounds which are useful as estrogenic agents. These include those of the formulas IV and V, below:

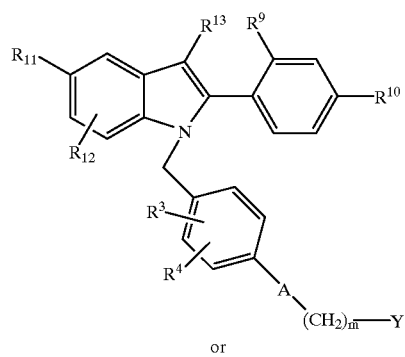

(IV)

or

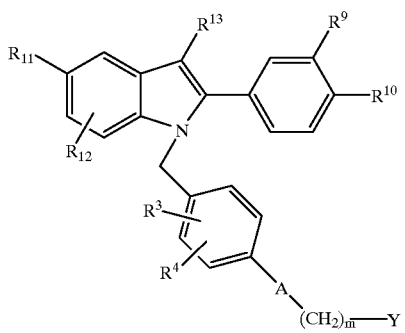

(V)

wherein:

$R_{11}$ is selected from H, OH or the $C_1$–$C_{12}$ esters (straight chain or branched) or C1–C12 (straight chain or branched or cyclic) alkyl ethers thereof, or halogens; or halogenated ethers including trifluoromethyl ether and trichloromethyl ether.

$R^{12}$, $R^9$, and $R^{10}$ are independently selected from H, OH or the $C_1$–$C_{12}$ esters (straight chain or branched) or C1–C12 alkyl ethers (straight chain or branched or cyclic) thereof, halogens, or halogenated ethers including triflouromethyl ether and trichloromethyl ether, cyano, $C_1$–$C_6$ allyl (straight chain or branched), or trifluoromethyl, with the proviso that, when $R_1$ is H, $R_2$ is not OH.

$R^{13}$ is selected from H, $C_1$–$C_6$ alkyl, cyano, nitro, trifluoromethyl, halogen; and Y, A, m, $R^3$ and $R^4$ are as defined herein.

The 2-Phenyl-1-[4(2-aminoethoxy)-benzyl]-indole compounds of this type are partial estrogen agonists and display high affinity for the estrogen receptor. Unlike many estrogens, however, these compounds do not cause increases in uterine wet weight. These compounds are antiestrogenic in the uterus and can completely antagonize the trophic effects of estrogen agonists in uterine tissue. These compounds are useful in treating or preventing in a mammal disease states or syndromes which are caused or associated with an estrogen deficiency.

These compounds have the ability to behave like estrogen agonists by lowering cholesterol and preventing bone loss. Therefore, these compounds are useful for treating many maladies including osteoporosis, prostatic hypertrophy, infertility, breast cancer, endometrial cancer, cardiovascular disease, contraception, Alzheimer's disease and melanoma Additionally, these compounds can be used for hormone replacement therapy in post-menopausal women or in other estrogen deficiency states where estrogen supplementation would be beneficial.

The 2-Phenyl-1-[4(2-aminoethoxy)-benzyl]-indole compounds produced with the compounds of this invention may also be used in methods of treatment for bone loss, which may result from an imbalance in a individual's formation of new bone tissues and the resorption of older tissues, leading to a net loss of bone. Such bone depletion results in a range of individuals, particularly in post-menopausal women, women who have undergone hysterectomy, those receiving or who have received extended corticosteroid therapies, those experiencing gonadal dysgenesis, and those suffering from Cushing's syndrome. Special needs for bone replacement can also be addressed using these compounds in individuals with bone fractures, defective bone structures, and those receiving bone-related surgeries and/or the implantation of prosthesis. In addition to those problems described above, these compounds can be used in treatments for osteoarthritis, Paget's disease, osteomalacia, osteohalisteresis, endometrial cancer, multiple myeloma and other forms of cancer having deleterious effects on bone tissues. Methods of treating the maladies listed herein are understood to comprise administering to an individual in need of such treatment a pharmaceutically effective amount of one or more of the compounds of this invention or a pharmaceutically acceptable salt thereof. This invention also includes pharmaceutical compositions utilizing one or more of the present compounds, and/or the pharmaceutically acceptable salts thereof, along with one or more pharmaceutically acceptable carriers, excipients, etc.

It is understood that the dosage, regimen and mode of administration of these 2-Phenyl-1-([(2-aminoethoxy)-benzyl]-indole compounds will vary according to the malady and the individual being treated and will be subject to the judgement of the medical practitioner involved. It is preferred that the administration of one or more of the compounds herein begin at a low dose and be increased until the desired effects are achieved.

Effective administration of these compounds may be given at a dose of from about 0.1 mg/day to about 1,000 mg/day. Preferably, administration will be from about 50 mg/day to about 600 mg/day in a single dose or in two or more divided doses. Such doses may be administered in any manner useful in directing the active compounds herein to the recipient's bloodstream, including orally, parenterally (including intravenous, intraperitoneal and subcutaneous injections), and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations herein may be utilize standard delay or time release formulations to alter the absorption of the active compound(s). Suppository formulations may be made from traditional materials, including cocoa butter, with or without the addition of waxes to alter the suppository's melting point, and glycerin. Water soluble suppository bases, such as polyethylene glycols of various molecular weights, may also be used.

As shown in Scheme VI, compounds of this group can be synthesized by allylation of the indole nitrogen with compounds of the present invention, as illustrated in Examples 11–13, below, utilizing (4-Chloromethyl-phenoxy)-ethyl-piperidin-1-yl hydrochloride of Example 8, (4-Chloromethyl-phenoxy)-ethyl-hexamethyleneimine-1-yl hydrochloride of Example 9 and (4-Chloromethyl-phenoxy)-ethyl-dimethylamino hydrochloride of Example 10, respectively. In addition to NaH, other bases may be used, including potassium t-butoxide or sodium t-butoxide.

Scheme VI
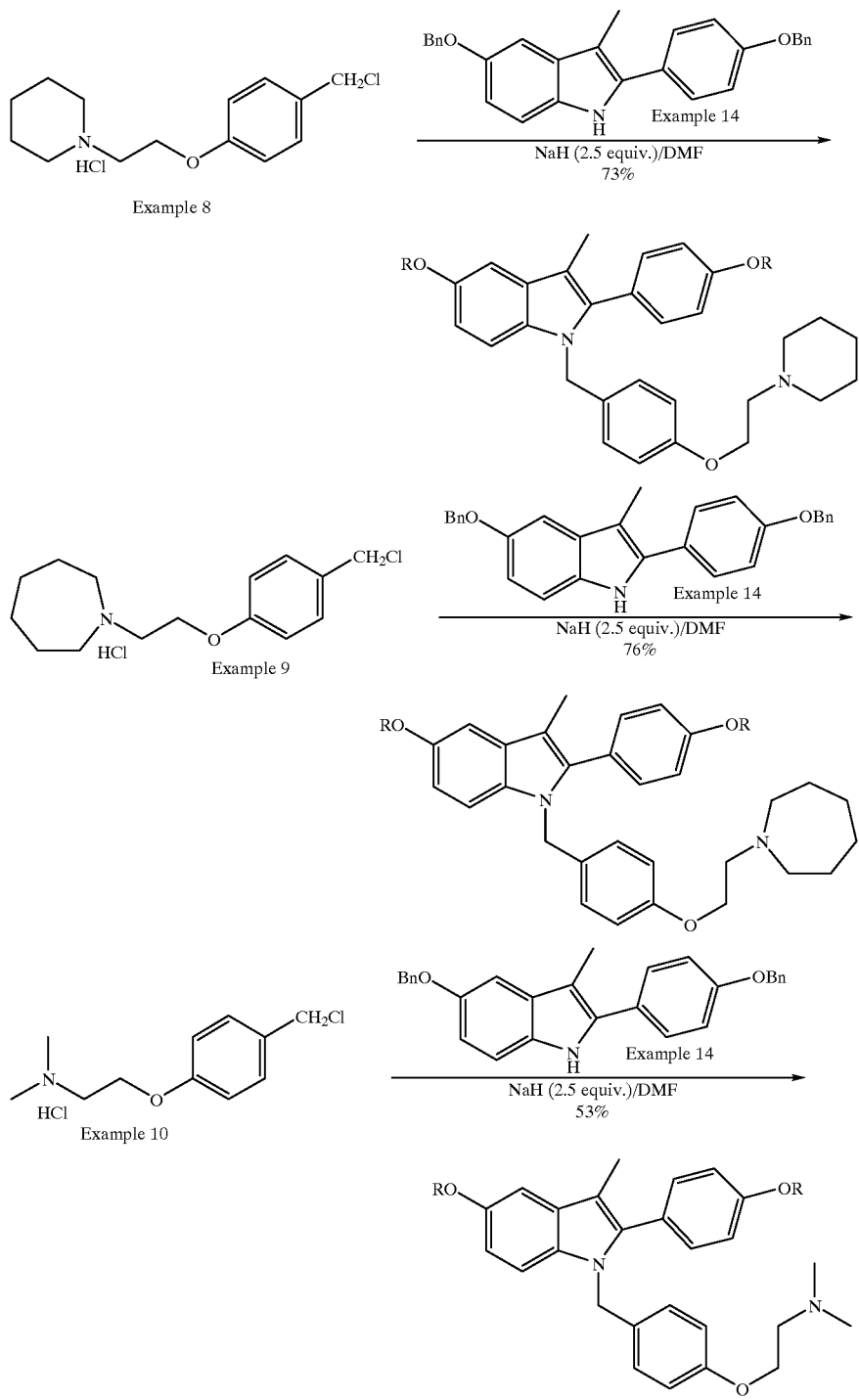
Schemes VII and VIII exemplify the synthesis of 1-[4-(2-Azepan-1-yl-ethoxy)-benzyl]2-(4-hydroxy-phenyl)-3-methyl-1H-indol-5-ol hydrochloride using intermediates of the present invention.

Scheme VII

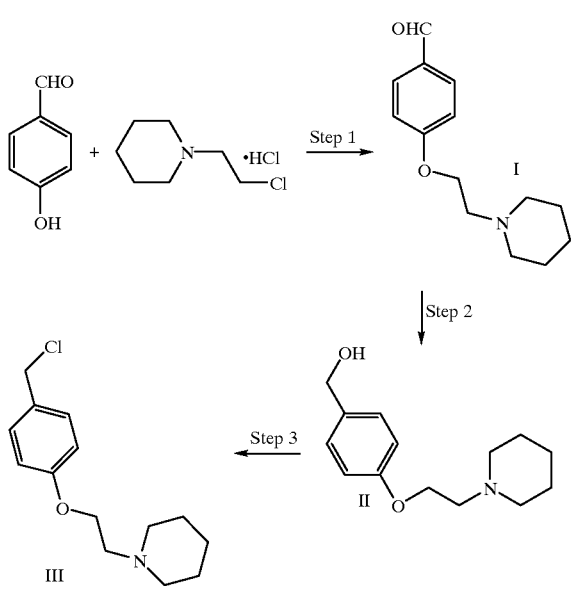

Scheme VII illustrates the alkylation of 4hydroxybenzaldehyde with 2-(hexamethylamino)ethyl chloride hydrochloride, which can be accomplished in the presence of potassium carbonate to give corresponding aldehyde I (Step 1). When the reaction is complete the mixture may be clarified, mixed with toluene and washed with water. The toluene solution can then be concentrated and the resulting residue treated with isopropanol to give a solution of aldehyde I. The isopropanol solution of I may be treated to catalytic reduction, such as with Raney Nickel, to yield alcohol II (Step 2). Following reduction, the reaction mixture may be clarified and concentrated, with the resulting residue being dissolved in ethylene dichloride to give a solution containing alcohol II. This solution may be treated with thionyl chloride, followed by concentration. The resulting residue can then be treated with 1,2 dimethoxyethane to yield crystalline III (Step 3).

Scheme VIII

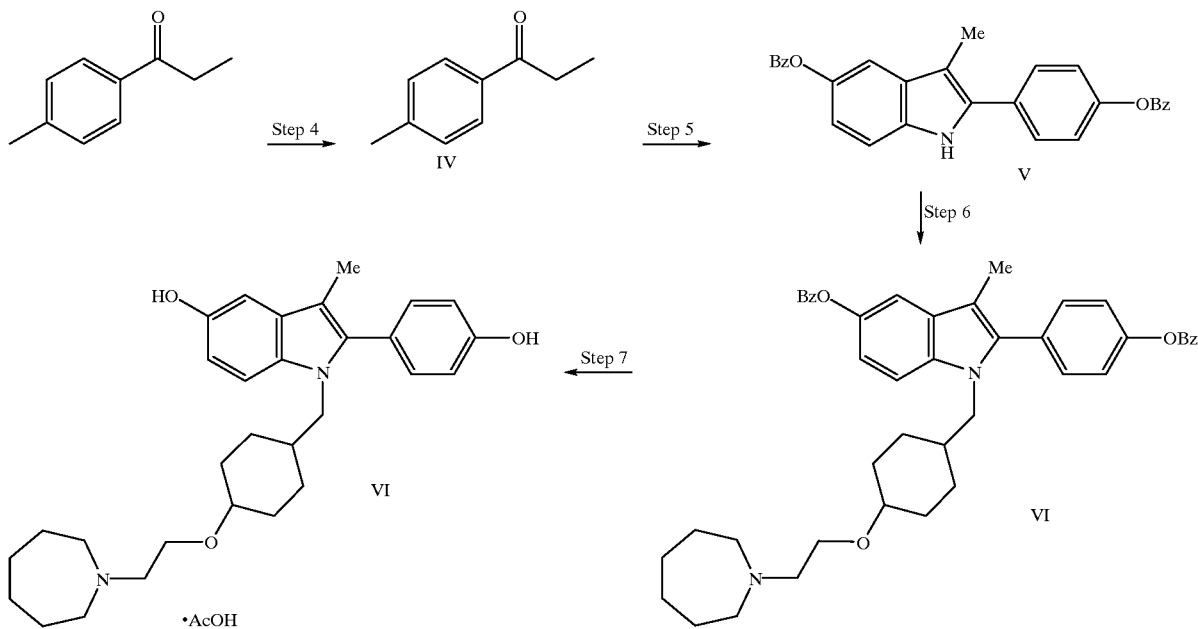

In Scheme VII, Step 4, 4-Benzyloxypropiophenone is brominated in acetic acid with bromine. When the reaction is complete the mixture can be quenched with water and the resulting precipitate is washed with dilute acetic acid, water and heptane. The resulting solid is dried to give IV, 4-benzyloxyaniline hydrochloride. In Step 5, a mixture of IV, N,N-diisopropylethylaiiine and toluene is heated under reflux with removal of water. When the reaction is complete the mixture may be cooled and diluted with methanol. The solids produced can be collected, washed with methanol and dried to give compound indole V. A mixture of compounds V and III can be mixed in Step 6 with sodium tert-butoxide in N,N-dimethylformamide and stirred until the reaction is complete. Then the mixture may be quenched with brine and extracted with toluene. The extracts are concentrated and the residue diluted with methanol. The resulting solids may be collected, dissolved in ethyl acetate, clarified, and diluted with methanol. The solids may be collected from this dilution and dried to give compound VI.

In a Step 7 (not shown) compound VI in a solution of ethanol can be hydrogenated with a Pd-charcoal catalyst. Following clarification, the hydrogenated material may be mixed with a small amount of ascorbic acid and treated with acetic acid. The resulting crystalline precipitate can then be collected, washed with ethanol and dried to give the final product, 1-[4-(2-Azepan-1-yl-ethoxy)-benzyl]2-(4-hydroxy-phenyl)-3-methyl-1H-indol-5-ol hydrochloride. The product may then be recrystallized from ethanol, optionally containing a small amount of ascorbic acid, preferably such as from about 0.5% by weight to about 3.0% by weight.

In the descriptions above, intermediates III through VI may be readily isolated as solids. All other intermediates may be more preferably used as solutions in organic solvents.

Schemes IX through XII exemplify the synthesis of 2-(4-Hydroxy-phenyl)-3-methyl-1-[4-(2-piperidin-1-yl-ethoxy)-benzyl]-1H-indol-5-ol utilizing intermediates of the present invention. Scheme IIa, described above, can be considered the first step of Scheme IX or a step prior thereto. In this step 4hydroxybenzyl alcohol is treated with a desired aryl amino alkyl chloride to afford the corresponding alkoxy benzyl alcohol. In the specific example of Scheme IIa, 4-hydroxybenzyl alcohol is treated with 1-(2-chloroethyl)-piperidine hydrochloride in the presence of $K_2CO_3/Me_2CO$ to yield 4-(2-piperidinylethoxy)benzyl alcohol. Toluene and brine can be added to the resulting alcohol mixture to separate its phases. The toluene phase can then be washed successively with aqueous alkali and brine. The resulting batch can then be concentrated and ethylene dichloride added to form a solution of the intermediate, 4-(2-piperidinylethoxy)benzyl alcohol.

The solution of 4-(2-piperidinylethoxy)benzyl alcohol in ethylene dichloride can be combined with thionyl chloride and heated until the reaction is complete. Upon cooling, the mixture can be concentrated, followed by addition of 1,2-dimethoxyethane and additional concentration. The precipitate can be collected and dried to yield intermediate 4-(2-piperidinylethoxy)benzylchloride hydrochloride, as shown in Scheme IX.

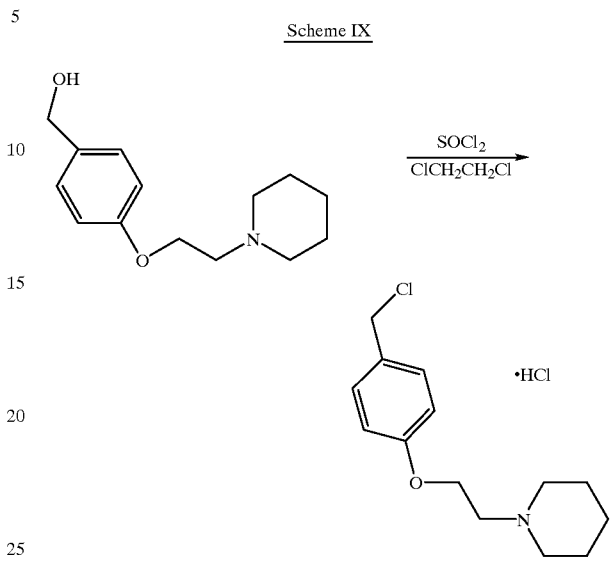

Scheme IX

As shown in Scheme IX, a solution of 4-(2-piperidinylethoxy)benzyl alcohol can be combined with ethylene dichloride and thionyl chloride and heated to create a reaction mixture. Upon cooling, the reaction mixture can be treated with 1,2-dimethoxyethane and concentrated, again. The resulting precipitate, 4-(2-piperidinylethoxy)benzylchloride hydrochloride, can then be collected and dried.

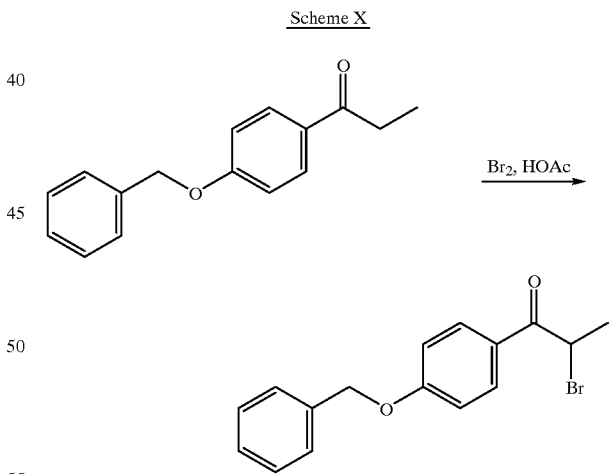

Scheme X

Scheme X depicts the bromination of 4-benzyloxypropiophenone in acetic acid with bromine to yield 4'-(benzyloxy)-2-bromopropiophenone. When this reaction is complete, the mixture can be quenched with water. The resulting precipitate can be collected, washed with dilute acetic acid, water and heptane, and dried.

Scheme XI

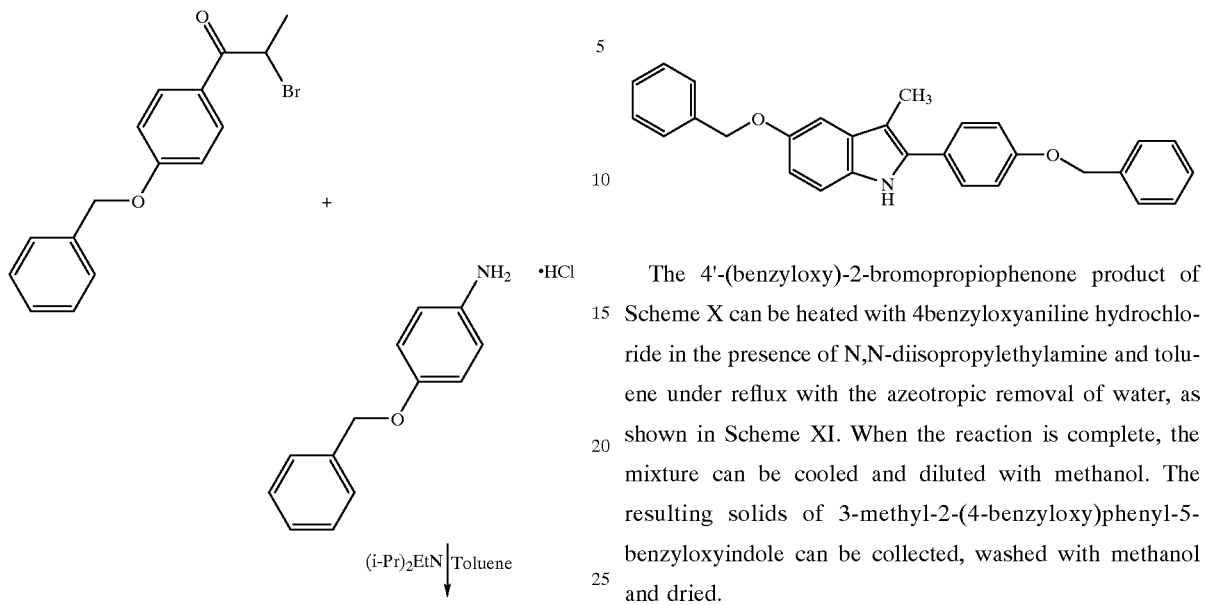

The 4'-(benzyloxy)-2-bromopropiophenone product of Scheme X can be heated with 4benzyloxyaniline hydrochloride in the presence of N,N-diisopropylethylamine and toluene under reflux with the azeotropic removal of water, as shown in Scheme XI. When the reaction is complete, the mixture can be cooled and diluted with methanol. The resulting solids of 3-methyl-2-(4-benzyloxy)phenyl-5-benzyloxyindole can be collected, washed with methanol and dried.

Scheme XII

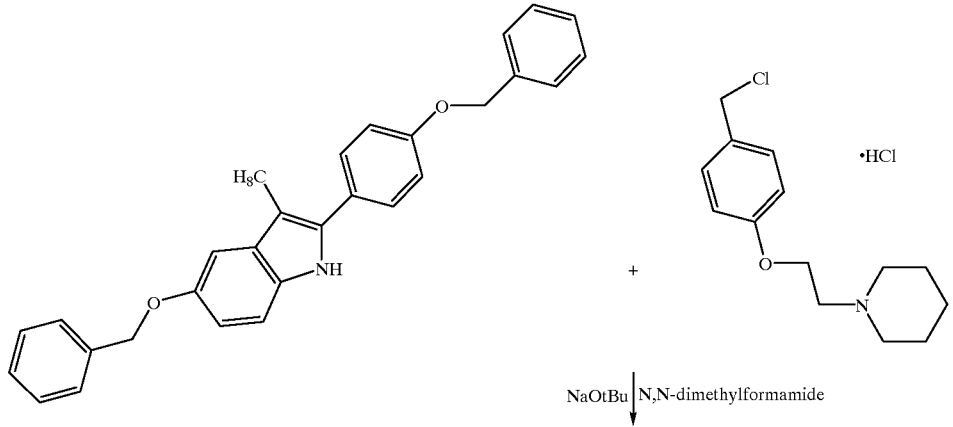

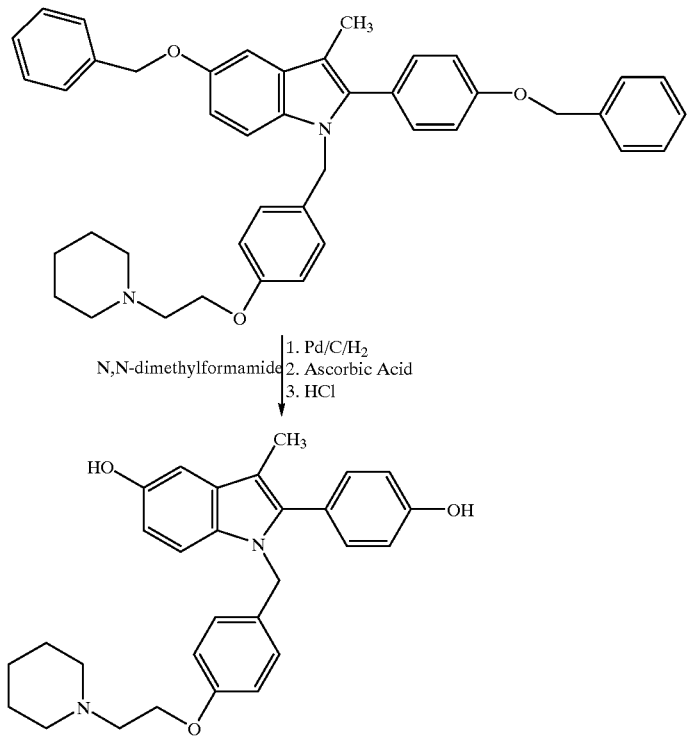

The 3-methyl-2-(4-benzyloxy)phenyl-5-benzyloxyindole product of Scheme XI can then be reacted with 4-(2-piperidinylethoxy)benzylchloride hydrochloride in the presence of sodium tert-butoxide in N,N-dimethylformamide. The resulting mixture can be quenched with brine and extracted with toluene. Following clarification, the extracts can be concentrated and diluted with methanol. The resulting solids of 5-Benzyloxy-2-(4-benzyloxyphenyl)-1-[4-(2-piperidin- 1-yl-ethoxy)benzyl]-1H-indole can be collected, dissolved in ethyl acetate and diluted with methanol and dried. These solids can be dissolved in ethanol-tetrahydrofuran and hydrogenated using Pd-charcoal catalyst. The solution may then be clarified, optionally mixed with a small amount of ascorbic acid and then treated with aqueous HCl. The precipitate can then be collected, washed with ethanol-tetrahydrofuran and water and dried to yield the final product, of 2-(4-Hydroxy-phenyl)-3-methyl-1-[4-(2-piperidin- 1-yl-ethoxy)-benzyl]-1H-indol-5-ol.

EXAMPLE 11

5-Benzyloxy-2-(4-benzyloxy-phenyl)-3-1-[4-(2-piperidin-1-yl-ethoxy)-benzyl]-1H-indole To a solution of 5-Benzyloxy-2-(4-benzyloxy-phenyl)-3-methyl-1H-indole (117.5 g, 0.28 mol, 1.0 eq.) in DMF (1.3 L), NaH (28.0 g, 60% oil dispersion, 0.7 mol, 2.5 eq.) was added in portions at −5/−8° C. over 1 h. The reaction mixture was stirred for 2 h. A solution of the chloride from Example 8 in THF (1.0 L) was added dropwise at −10/0° C. over 2 h. The reaction mixture was stirred at 25° C. overnight. TLC at this point showed no starting material, mostly product (EtOAc/hexane 1:5). The reaction mixture was diluted with water (6 L), extracted with EtOAc (2×3 L), and dried over Na$_2$SO$_4$. The solution was concentrated to 1 L, poured in MeOH (2.5 L), and stirred for 1 h. The precipitate was filtered and dried to give the title compound (129 g, 73%).

$^1$H NMR (CDCl$_3$/TMS): 7.64–6.63 (m, 21H), 5.12 (s, 2H), 5.09 (s, 2H), 5.07 (s, 2H), 4.07 (t, 2H, J=6.06 Hz), 2.72 (t, 2H, J=6.06 Hz), 2.48 (m, 4H), 2.24 (s, 3H), 1.62–1.24 (m, 6H).

EXAMPLE 12

5-Benzyloxy-2-(4-benzyloxy-phenyl)-3-1-[4-(2-hexamethyleneimine-1-yl-ethoxy)-benzyl]-1H indole To a slurry of NaH (20.0 g, 60% oil dispersion, 0.5 mol, 2.5 eq.) solution of 5-Benzyloxy-2-(4benzyloxy-phenyl)-3-methyl-1H-indole (84 g, 0.2 mol, 1.0 eq.) in DMF (100 mL) was added at 0/+10° C. over 1 h. The reaction mixture was stirred for 30 min. A solution of the chloride from Example 9 (67 g, 0.22 mol, 1.1 eq.)in DMF (200 mL) was added dropwise at 0/+10° C. over 2 h. The reaction mixture was stirred at 25° C. for 2 h. TLC at this point showed no starting material, mostly product (EtOAc/hexane 1:5). The reaction mixture was diluted with water (1 L), extracted with EtOAc (3×1 L), and dried over MgSO$_4$. The solution was concentrated to 150 mL, poured in MeOH (750 mL), and stirred overnight. The precipitate was filtered and dried to give the title compound (99 g, 76%).

$^1$H NMR (CDCl$_3$/TMS): 7.48–6.74 (m, 21H), 5.13 (s, 2H), 5.11 (s, 2H), 5.09 (s, 2H), 4.00 (t, 2H, J=6.24 Hz), 2.91 (t, 2H, J=6.27 Hz), 2.75 (m, 4H), 2.24 (s, 3H), 1.71–1.52 (m, 8H)

EXAMPLE 13

5-Benzyloxy-2-(4-benzyloxy-phenyl)-3-1-[4-(2-dimethylaminoethoxy)-benzyl]-1H indole To a slurry of NaH (1. 1 g, 60% oil dispersion, 0.05 mol, 2.5 eq.) solution of indole was added 5-Benzyloxy-2-

(4benzyloxy-phenyl)-3-methyl-1H-indole (6.97 g, 0.017 mol, 1.0 eq.) in DMF (100 mL) at 0/+10° C. over 0.5 h. The reaction mixture was stirred for 30 min. A solution of the chloride from Example 10 (4.57 g, 0.018 mol, 1.1 eq.) was added portionwise at 0/+10° C. over 2 h. The reaction mixture was stirred at 25° C. for 0.5 h. TLC at this point showed no starting material, mostly product (EtOAc/hexane 1:5). The reaction mixture was diluted with water (200 mL), extracted with EtOAc (3×200 mL), and dried over MgSO$_4$. The solution was concentrated to 150 mL, poured in MeOH (300 mL), and stirred overnight. The precipitate was filtered and dried to give the title compound 5.6 g (53%).

1H NMR (CDCl$_3$/TMS): 7.50–6.66 (m, 21H), 5.13 (s, 2H), 5.11 (s, 2H), 5.09 (s, 2H), 3.99 (t, 2H, J=5.76 Hz), 2.69 (t, 2H, J=5.73 Hz), 2.31 (s, 6H), 2.42 (s, 3H)

EXAMPLE 14

5-Benzyloxy-2-(4-benzyloxy-phenyl)-3-methyl-1H-indole

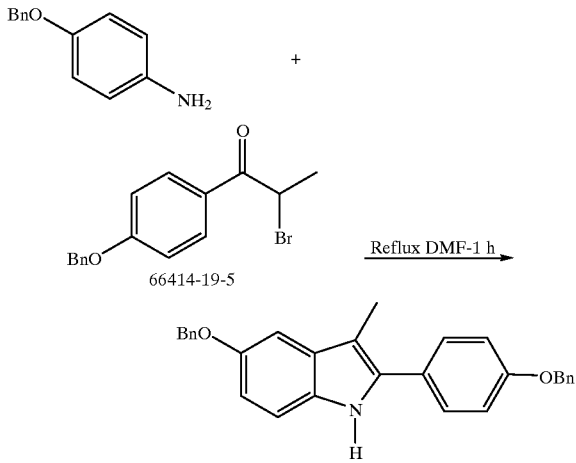

A flask was charged with 4-benzyloxyaniline (45 g, 0.23 mol), 4'-benzyloxy-2-bromophenylpropiophenone (66414-19-5) (21 g, 0.066 mol), and 50 mL DMF. The reaction was heated at reflux for 30 minutes and then cooled to rt and then partitioned between 250 mL EtOAc and 100 mL 1N HCl (aq). The EtOAc was washed with NaHCO$_3$ (aq) and brine, dried over MgSO$_4$. The solution was concentrated and the residue taken up in CH$_2$Cl$_2$ and hexanes added to precipitate out 25 g of a crude solid. The solid was dissolved in CH$_2$Cl$_2$ and evaporated onto silica gel and chromatographed using CH$_2$Cl$_2$/Hexane (1:5) to yield 9.2 g of a tan solid (33%): Mpt=150–152° C.;

$^1$H NMR (DMSO) 10.88 (s, 1 H), 7.56 (d, 2 H, J=8.8 Hz), 7.48 (d, 4 H, J=7.9 Hz), 7.42–7.29 (m, 6 H), 7.21 (d, 1 H, J=7.0 Hz), 7.13 (d, 2 H, J=8.8 Hz), 7.08 (d, 1 H, J=2.2 Hz), 6.94 (dd, 1 H, J=8.8, 2.4 Hz), 5.16 (s, 2H), 5.11 (s, 2 H), 2.33.(s, 3 H); IR (KBr) 3470, 2880, 2820, 1620 cm$^{-1}$; MS eI m/z 419.

EXAMPLE 15

2-(4-Hydroxy-phenyl)-3-methyl-1-[4-(2-piperidin-1-yl-ethoxy)-benzyl]-1H-indol-5-ol A suspension of 10% Pd/C (1.1 g) in EtOH was treated with a solution of the title compound of Example 11 (2.2 g, 3.4 mmol) in THF/EtOH. Cyclohexadiene (6.0 mL, 63 mmol) was added and the reaction was stirred for 48 hours. The catalyst was filtered through Celite and the reaction mixture was concentrated and chromatographed on silica gel using a gradient elution of MeOH(CH$_2$Cl$_2$ (1:19 to 1:10) to yield 0.8 g of the product as a white solid. Mpt=109–113° C.; CHN calc'd for C$_{29}$H$_{32}$N$_2$O$_3$+0.5 H$_2$O;

$^1$H NMR 9.64 (s, 1 H), 8.67 (s, 1 H), 7.14 (d, 2 H, J=8.6 Hz), 7.05 (d, 1 H, J=8.6 Hz), 6.84 (d, 2 H, J=8.8 Hz), 6.79 (d, 1 H, J=2.2 Hz), 6.74 (s, 4 H), 6.56 (dd, 1 H, J=8.8, 2.4 Hz), 5.09 (s, 2 H), 3.95–3.93 (m, 2 H), 2.60–2.51 (m, 2 H), 2.39–2.38 (m, 4 H), 2.09 (s, 3 H), 1.46–1.45 (m, 4 H), 1.35–1.34 (m, 2 H); IR (KBr) 3350 (br), 2920, 1620, 1510 cm–1; MS (EI) m/z 456.

In Vitro Estrogen Receptor Binding Assay

Receptor Preparation

CHO cells overexpressing the estrogen receptor were grown in 150 mm$^2$ dishes in DMEM+10% dextran coated charcoal, stripped fetal bovine serum. The plates were washed twice with PBS and once with 10 mM Tris-HCl, pH 7.4, 1 mM EDTA. Cells were harvested by scraping the surface and then the cell suspension was placed on ice. Cells were disrupted with a hand-held motorized tissue grinder using two, 10-second bursts. The crude preparation was centrifuged at 12,000 g for 20 minutes followed by a 60 minute spin at 100,000 g to produce a ribosome free cytosol. The cytosol was then frozen and stored at −80° C. Protein concentration of the cytosol was estimated using the BCA assay with reference standard protein.

Binding Assay Conditions

The competition assay was performed in a 96-well plate (polystyrene*) which binds <2.0% of the total input [$^3$H]-17__-estradiol and each data point was gathered in triplicate. 100 uG/100 uL of the receptor preparation was aliquoted per well. A saturating dose of 2.5 nM [$^3$H]17__-estradiol+ competitor (or buffer) in a 50 uL volume was added in the preliminary competition when 100× and 500× competitor were evaluated, only 0.8 nM [$^3$H]17__-estradiol was used. The plate was incubated at room temperature for 2.5 h. At the end of this incubation period 150 uL of ice-cold dextran coated charcoal (5% activated charcoal coated with 0.05% 69K dextran) was added to each well and the plate was immediately centrifuged at 99 g for 5 minutes at 4° C. 200 uL of the supernatant solution was then removed for scintillation counting. Samples were counted to 2% or 10 minutes, whichever occurs first. Because polystyrene absorbs a small amount of [$^3$H]17__-estradiol, wells containing radioactivity and cytosol, but not processed with charcoal were included to quantitate amounts of available isotope. Also, wells containing radioactivity but no cytosol were processed with charcoal to estimate unremovable DPM of [$^3$H]17__-estradiol. Corning #25880-96, 96-well plates were used because they have proven to bind the least amount of estradiol.

Analysis of Results

Counts per minute (CPM) of radioactivity were automatically converted to disintegrated per minute (DPM) by the Beckman LS 7500 Scintillation Counter using a set of quenched standards to generate a H# for each sample. To calculate the % of estradiol binding in the presence of 100 or fold 500 fold competitor the following formula was applied:

((DPM sample—DPM not removed by charcoal/(DPM estradiol—DPM not removed by charcoal))×100%=% of estradiol binding For the generation of IC$_{50}$ curves, % binding is plotted vs compound. IC$_{50}$'s are generated for compounds that show >30% competition at 500× competitor concentration. For a description of these methods, see Hulme, E. C., ed. 1992. Receptor-Ligand Interactions: A Practical Approach. IRL Press, New York.(see especially chapter 8). Reference in the tables below to the compound of Example 1 refer to the final product, 2-(4-Hydroxy-phenyl)-3-methyl-1-[4-(2-piperidin-1-yl-ethoxy)-benzyl]-1H-indol-5-ol.

| Estrogen Receptor Affinity (reported as RBA: 17_-estradiol = 100) | |
|---|---|
| Compound | RBA |
| Raloxifene | 200 |
| Tamoxifen | 1.8 |
| Equilin | 5.3 |
| Example 15 | 400 |

Ishikawa Cell Alkaline Phosphatase Assay

Cell Maintenance and Treatment

Ishikawa cells were maintained in DMEM/F12 (50%:50%) containing phenol red+10% fetal bovine serum and the medium was supplemented with 2 mM Glutamax, 1% Pen/Strap and 1 mM sodium pyruvate. Five days prior to the beginning of each experiment (treatment of cells) the medium was changed to phenol red-free DMEM/F12+10% dextran coated charcoal stripped serum. On the day before treatment, cells were harvested using 0.5% trypsin/EDTA and plated at a density of $5 \times 10^4$ cells/well in 96-well tissue culture plates. Test compounds were dosed at $10^{-6}$, $10^{-7}$ and $10^{-8}$ M in addition to $10^{-6}$ M (compound)+$10^{-9}$ M 17_-estradiol to evaluate the ability of the compounds to function as antiestrogens. Cells were treated for 48 h prior to assay. Each 96-well plate contained a 17_-estradiol control. Sample population for at each dose was n=8.

Alkaline Phosphatase Assay

At the end of 48 h the media is aspirated and cells are washed three times with phosphate buffered saline (PBS). 50_L of lysis buffer (0.1 M Tris-HCl, pH 9.8, 0.2% Triton X-100) is added to each well. Plates are placed at –80° C. for a minimum of 15 minutes. Plates are thawed at 37° C. followed by the addition of 150_L of 0.1 M Tris-HCl, pH 9.8, containing 4 mM para-nitrophenylphosphate (pNPP) to each well (final concentration, 3 mM pNPP). Absorbance and slope calculations were made using the KineticCalc Application program (Bio-Tek Instruments, Inc., Winooski, Vt.). Results are expressed as the mean +/–S.D. of the rate of enzyme reaction (slope) averaged over the linear portion of the kinetic reaction curve (optical density readings every 5 minutes for 30 minutes absorbance reading). Results for compounds are summarized as percent of response related to 1 nM 17_estradiol. Various compounds were assayed for estrogenic activity by the alkaline phosphatase method and corresponding ED50 values (95% C.I.) were calculated. The four listed in the following were used as reference standards:

| 17_-estradiol | 0.03 nM | 17_-estradiol | 1.42 nM |
|---|---|---|---|
| estriol | 0.13 nM | estrone | 0.36 nM |

A description of these methods is described by Holinka, C. F., Hata, H., Kuramoto, H. and Gurpide, E. (1986) Effects of steroid hormones and antisteroids on alkaline phosphatase activity in human endometrial cancer cells (Ishikawa Line). Cancer Research, 46:2771–2774, and by Littlefield, B. A., Gurpide, E., Markiewicz, L., McKinley, B. and Hochberg, R. B. (1990) A simple and sensitive microtiter plate estrogen bioassay based on stimulation alkaline phosphatase in Ishikawa cells; Estrogen action of D5 adrenal steroids. Endocrinology, 6:2757–2762.

| Ishikawa Alkaline Phosphatase Assay | |
|---|---|
| Compound | % Activation |
| 17_-estradiol | 100% activity |
| tamoxifen | 0% activity (45% with 1 nM 17_-estradiol) |
| raloxifene | 5% activity (5% with 1 nM 17_-estradiol) |
| Example 15 | 1% activity (1% with 1 nM 17_-estradiol) |

2X VIT ERE Transfection Assay

Cell Maintenance and Treatment

Chinese Hamster Ovary cells (CHO) which had been stably transfected with the human estrogen receptor were maintained in DMEM+10% fetal bovine serum (FBS). 48 h prior to treatment the growth medium was replaced with DMEM lacking phenol red+10% dextran coated charcoal stripped FBS (treatment medium). Cells were plated at a density of 5000 cells/well in 96-well plates containing 200_L of medium/well.

Calcium Phosphate Transfection

Reporter DNA (Promega plasmid pGL2 containing two tandem copies of the vitellogenin ERE in front of the minimal thymidine kinase promoter driving the luciferase gene) was combined with the B-galactosidase expression plasmid pCH110 (Pharmacia) and carrier DNA (pTZ18U) in the following ratio:

10 uG of reporter DNA 5 uG of pCH110 DNA 5 uG of pTZ18U 20 uG of DNA/1 mL of transfection solution The DNA (20 uG) was dissolved in 500 uL of 250 mM sterile $CaCl_2$ and added dropwise to 500 uL of 2×HeBS (0.28 M NaCl, 50 mM HEPES, 1.5 mM $Na_2HPO_4$, pH 7.05) and incubated at room temperature for 20 minutes. 20 uL of this mixture was added to each well of cells and remained on the cells for 16 h. At the end of this incubation the precipitate was removed, the cells were washed with media, fresh treatment media was replaced and the cells were treated with either vehicle, 1 nM 17_-estradiol, 1 uM compound or 1 uM compound+1 nM 17_-estradiol (tests for estrogen antagonism). Each treatment condition was performed on 8 wells (n=8) which were incubated for 24 h prior to the luciferase assay.

Luciferase Assay

After 24 h exposure to compounds, the media was removed and each well washed with 2× with 125 uL of PBS lacking Mg++ and Ca++. After removing the PBS, 25 uL of Promega lysis buffer was added to each well and allowed to stand at room temperature for 15 min, followed by 15 min at –80° C. and 15 min at 37° C. 20 uL of lysate was transferred to an opaque 96 well plate for luciferase activity evaluation and the remaining lysate (5 uL) was used for the B-galactosidase activity evaluation (nonnalize transfection). The luciferan substrate (Promega) was added in 100 uL aliquots to each well automatically by the luminometer and the light produced (relative light units) was read 10 seconds after addition.

| Infection Luciferase Assay | |
|---|---|
| Compound | % Activation |
| 17_-estradiol | 100% activity |
| estriol | 38% activity |
| tamoxifen | 0% activity (10% with 1 nM 17_-estradiol) |
| raloxifene | 0% activity (0% with 1 nM 17_-estradiol) |
| Example 15 | 0% activity (0% with 1 nM 17_-estradiol) |

B-Galactosidase Assay

To the remaining 5 uL of lysate 45 uL of PBS was added. Then 50 uL of Promega B-galactosidase 2× assay buffer was added, mixed well and incubated at 37° C. for 1 hour. A plate containing a standard curve (0.1 to 1.5 milliunits in triplicate) was set up for each experimental run. The plates were analyzed on a Molecular Devices spectrophotometric plate reader at 410 nm. The optical densities for the unknown were converted to milliunits of activity by mathematical extrapolation from the standard curve.

Analysis of Results

The luciferase data was generated as relative light units (RLUs) accumulated during a 10 second measurement and automatically transferred to a JMP (SAS Inc) file where background RLUs were subtracted. The B-galactosidase values were automatically imported into the file and these values were divided into the RLUs to normalize the data. The mean and standard deviations were determined from a n=8 for each treatment. Compounds activity was compared to 17_-estradiol for each plate. Percentage of activity as compared to 17_-estradiol was calculated using the formula %=((Estradiol-control)/(compound value))×100. These techniques are described by Tzukerman, M. T., Esty, A., Santiso-Mere, D., Danielian, P., Parker, M. G., Stein, R. B., Pike, J. W. and McDonnel, D. P. (1994). Human estrogen receptor transactivational capacity was determined by both cellular and promoter context and mediated by two functionally distinct intramolecular regions (see Molecular Endocrinology, 8:21–30).

Rat Uterotrophic/Antiuterotrolphic Bioassay

The estrogenic and antiestrogenic properties of the compounds were determined in an immature rat uterotrophic assay (4 day) that (as described previously by L. J. Black and R. L. Goode, Life Sciences, 26, 1453 (1980)). Immature Sprague-Dawley rats (female, 18 days old) were tested in groups of six. The animals were treated by daily ip injection with 10 uG compound, 100 uG compound, (100 uG compound+1 uG 17_-estradiol) to check antiestrogenicity, and 1 uG 17_-estradiol, with 50% DMSO/50% saline as the injection vehicle. On day 4 the animals were sacrificed by $CO_2$ asphyxiation and their uteri were removed and stripped of excess lipid, any fluid removed and the wet weight determined. A small section of one horn was submitted for histology and the remainder used to isolate total RNA in order to evaluate complement component 3 gene expression.

| 3 day Ovariectomized Rat Model | | | |
|---|---|---|---|
| Compound | 10 uG | 100 uG | 100 uG + 1 uG 17_-estradiol |
| Tamoxifen | 69.6mg | 71.4mg | |
| Raloxifen | 47.5 | 43.2 | |
| control = 42.7 mg | | 1 uG 17_-estradiol = 98.2 | |
| Example 15 | 39.9mg | 27.4mg | 24.3 mg |
| control = 30.7 mg | | 1 uG 17_-estradiol = 63.2 | |

The compound Raloxifen [2-(4-hydroxyphenyl)-6-hydroxybenzo[b]thien-3-yl][-(1-piperidinyl0ethoxy]phenyl-methanone hydrochloride is representative of a class of compounds known to be selective estrogen receptor modulators, possessing estrogen agonist-like actions on bone tissues and scrum lipids while exhibiting estrogen antagonism in uterine and breast tisses. Palkowitz et al. suggest in J. Med. Chem 1997, 40, 1407 active analogs of Raloxifen which may also be produced utilizing the compounds of this invention. For instance, their disclosed compound 4a, [2-(4-hydroxyphenyl)-6hydroxybenzo[b]thien-3-yl][4(1-piperidinyl)ethoxy]phenyl-methane hydrochloride can be produced by the general reaction scheme below.

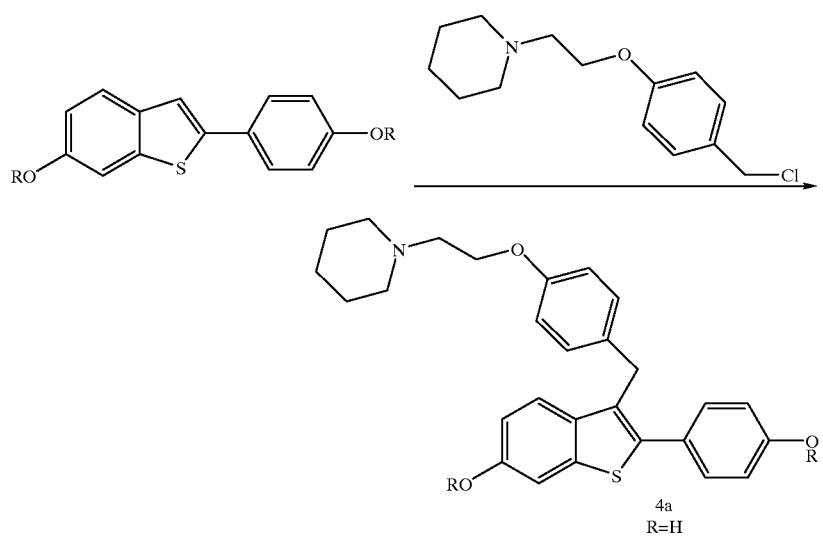

EXAMPLE 16

2-(4-Methoxy-benzenesulfonylamino)-benzoic acid methyl ester

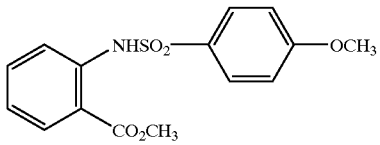

To a solution of 2.00 g (0.013 mol) of methyl anthranilate dissolved in 20 mL of chloroform was added 3.2 mL (0.039 mol) of pyridine followed by 2.733 g (0.013 mol) of p-methoxybenzenesulfonyl chloride. The reaction mixture was stirred at room temperature for 5 h and then washed with 3N HCl and water. The organics were then dried over $Na_2SO_4$, filtered and concentrated in vacuo. The resulting white solid was washed with ether and dried in vacuo to provide 3.7 g (87%) of the desired sulfonamide. CI Mass Spec: 322 (M+H).

EXAMPLE 17

2-(4-Methoxy-benzenesulfonylamino)-3-methyl-benzoic acid methyl ester

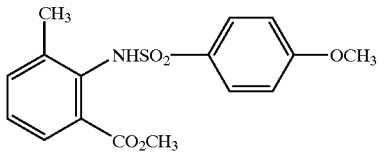

In the same manner as described in Example 16, 6.24 g (0.038 mol) of methyl-3-methyl-anthranilate provided 6.21 g (49%) of the desired sulfonamide as a white solid. Electrospray Mass Spec 336.2 (M+H).

EXAMPLE 18

4-(2-Piperidin-1-yl-ethoxy)-benzyl chloride

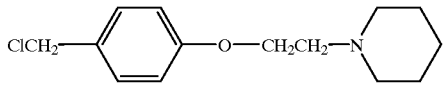

To a stirred solution of 4-hydroxy benzaldehyde (12.2 gm, 0.1 mol) and K2CO3 (25 gm, excess) in N,N-dimethlformamide (250 ml) was added 1-(2-chloroethyl)piperidine monohydrochloride (20.0 gm, 1.08 mol). The reaction mixture was heated to 80_C. for 24 hrs and cooled to room temperature. The reaction mixture was quenched with ice cold water and extracted with chloroform. The organics were washed with water, dried over anhydrous $MgSO_4$, filtered and concentrated in vacuo. The residue was dissolved in methanol and sodium borohydride (10 gms, excess) was slowly added at O_C. The reaction mixture was stirred at room temperature for 2 h and then quenched with water. The alcohol was extracted with chloroform, the organics were washed well with water, dried over $Na_2SO_4$, filtered and concentrated in vacuo.

The crude alcohol thus obtained was dissolved in THF (200 ml) and HCl gas was passed through for 30 minutes at O_C. To the suspension of hydrochloride thus obtained, thionyl chloride (30 ml, excess) was slowly added. The reaction mixture was refluxed for thirty minutes and cooled to room temperature. The reaction mixture was then concentrated to dryness and triturated with anhydrous ether. The precipitated solid was filtered and dried under vacuum at room temperature to give 25 g (86%) of the product as a white solid. m.p. 145 - 148_C. Electrospray Mass Spec: 256 (M+H).

EXAMPLE 19

4-(2-N,N-Diethyl-ethoxy)-benzyl chloride

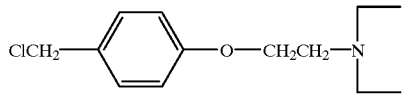

To a stirred solution of 4-hydroxy benzaldehyde (12.2 gm, 0.1 mol) and $K_2CO_3$ (25 gm, excess) in N,N-dimethlfornamide (250 ml) was added 2-diethyl-aminoethyl chloride monohydrochloride (20.0 gm, 1.2 mol). The reaction mixture was heated at 80_C. for 24 hrs and cooled to room temperature. The reaction mixture was quenched with ice cold water and extracted with chloroform. The organics were washed with water, dried over anhydrous $MgSO_4$, filtered and concentrated in vacuo. The residue was dissolved in methanol and sodium borohydride (10 gms, excess) was slowly added at O_C. The reaction mixture was stirred at room temperature for 2 h and then quenched with water. The alcohol was extracted with chloroform, washed well with water, dried, filtered and concentrated in vacuo.

The crude alcohol thus obtained was dissolved in THF (200 ml) and HCl gas was passed through for 30 minutes at O_C. To the suspension of hydrochloride thus obtained, thionyl chloride (30 ml, excess) was slowly added. The reaction mixture was refluxed for thirty minutes and cooled to room temperature. The reaction mixture was then concentrated to dryness and triturated with anhydrous ether. The precipitated solid was filtered and dried under vacuum at room temperature to give 18 g (65%) of the product as a white solid, m.p. 7–79_C. Electrospray Mass Spec: 244 (M+H).

EXAMPLE 20

N-Hydroxy-2-[[(4-methoxyphenyl)sulfonyl][[4-[2-(1-piperidinyl)ethoxy]phenyl]methyl]amino]-3-methylbenzamide To a solution of 1.00 g (2.985 mmol) of 2-(4-methoxy-benzene-sulfonylamino)-3-methyl-benzoic acid methyl ester in 5 ml of DMF was added 0.952 g (3.284 mmol) of 4-(2-piperidin-1-yl-ethoxy)benzyl chloride and 1.65 g (11.9 mmol) of potassium carbonate. The reaction mixture was then stirred at room temperature for 18 h, diluted with water and extracted with ether. The organics were then extracted with 6 N HCl solution and the aqueous acid layer was then basified with 6 N NaOH solution and then extracted with ether. The resulting ether layer was dried over sodium sulfate, filtered and concentrated in vacuo to provide 0.965 g of the piperidine-ester as a colorless oil. Electrospray Mass Spec: 553.5 $(M+H)^+$.

To a solution of 0.889 g (1.611 mmol) of piperidine ester in 7 ml of THF was added 0.203 g lithium hydroxide monohydrate. The resulting mixture was heated to reflux for 15 h, and then concentrated in vacuo to a residue. The residue was diluted with water, neutralized with 5% HCl solution and extracted with dichloromethane. The organic layer was dried over Na$_2$SO$_4$, filtered and concentrated in vacuo to provide 0.872 g of the carboxylic acid as a white foam. Electrospray Mass Spec: 539.2 (M+H)$^+$.

To a solution of 0.814 g (1.513 mmol) of the carboxylic acid in 10 ml of DMF was added 0.245 g (1.82 mmol) of HOBT and 0.386 g (2.01 mmol) of EDC. The reaction was then stirred for 1 h at room temperature and 0.46 ml (7.57 mmol) of a 50% solution of hydroxylamine in water was added. The reaction was stirred overnight and then concentrated in vacuo to a residue. The residue was diluted with EtOAc, washed with water and sodium bicarbonate solution, dried over Na$_2$SO$_4$, filtered and concentrated in vacuo to a residue. The residue was dissolved in 5 ml of dichloromethane and 0.69 ml of a 1 N solution of HCl in ether was added. After 1 h the reaction was diluted with ether and the resulting solid was filtered and dried in vacuo to give 0.179 g of the hydroxamate-amine salt as a white solid. Electrospray Mass Spec: 554.5 (M+H)$^+$.

EXAMPLE 21

2-[[4-(2-Diethylamino-ethoxy)-benzyl]-(4-methoxy-benzenesulfonyl)-amino]-N-hydroxy-3-methyl-benzamide To a solution of 1.0 g (2.653 mmol) of 2-(4-methoxybenzene-sulfonylamino)-3-methylbenzoic acid methyl ester in 10 ml of DMF was added 0.811 g (2.918 mmol) of 4-(2-N,N-diethyl-ethoxy)-benzyl chloride and 1.5 g (10.9 mmol) of potassium carbonate. The reaction mixture was then stirred at room temperature for 18 h, diluted with water and extracted with ether. The organics were then extracted with 6 N HCl solution and the aqueous acid layer was then basified with 6 N NaOH solution and then extracted with ether. The resulting ether layer was dried over sodium sulfate, filtered and concentrated in vacuo to provide 0.575 g (37%) of the N,N-diethylamino-ester as a tan foam. Electrospray Mass Spec: 583.1 (M+H)$^+$.

To a solution of 0.539 g (0.926 mmol) of the N,N-diethylamino-ester in dichloromethane was added 2 mL of trifluoroacetic acid. The reaction was stirred at room temperature for 2 h and then concentrated in vacuo to a residue. The residue was triturated with ether and the resulting solid was collected by filtration and dried in vacuo to give 0.369 g of the carboxylic acid as a white solid. Electrospray Mass Spec: 525.2 (M–H)$^-$.

To a solution of 0.328 g (0.513 mmol) the carboxylic acid in 6.5 ml of dichloromethane was added 0.12 ml of DMF followed by 0.77 ml of 2.0 M oxalyl chloride in CH$_2$Cl$_2$ and the reaction mixture was stirred at room temperature for 1 h.

In a separate flask was added at 0° C. to a mixture of 0.47 mL (7.7 mmol) of a 50% solution of hydroxylamine in water 8 ml of THF and 1.7 ml of water. After this mixture had stirred for 15 minutes at 0° C., the acid chloride solution was added to it in one portion and the resulting solution was allowed to warm to room temperature with stirring overnight. The reaction mixture was then acidified to pH 3 with 10% HCl and extracted with EtOAc. The combined organic layers were dried over Na$_2$SO$_4$, filtered and concentrated in vacuo to a residue. The residue is triturated with ether to provide 194 g of the hydroxamate-amine salt as a white solid. Electrospray Mass Spec: 42.3 (M+H)$^+$.

EXAMPLE 22

2-(4-Methoxy-phenylsulfanyl)-propionic acid ethyl ester

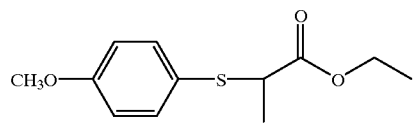

To a stirred solution of 4methoxybenzenethiol (2.5 gm, 14 mmol) and anhydrous K$_2$CO$_3$ (4.0 gm, excess) in dry acetone (100 ml), ethyl 2-bromo-propionate (3.0 gm, 16 mmol) was added in a round bottom flask and the reaction mixture was heated at reflux for 8 hours with good stirring. At the end, reaction was allowed to cool, filtered and the reaction mixture was concentrated to a residue. The residue was extracted with chloroform and washed with H$_2$O and the organic layer dried over MgSO$_4$, filtered and concentrated to afford 2-(4-methoxy-phenylsulfanyl)-propionic acid ethyl ester as a light yellow oil. Yield 3.6 gms (94%).

EXAMPLE 23

2-(4-Methoxy-benzenesulfonyl)-propionic acid ethyl ester

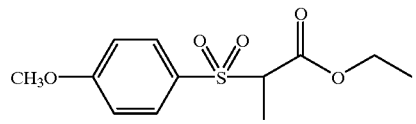

To a stirred solution of 12.0 gm (50 mmol) of 2-(4-methoxy-phenylsulfanyl)-propionic acid ethyl ester in 300 ml of methylene chloride at 0° C. was slowly added at a rate to control the exotherm. The reaction mixture was stirred at room temperature for 2 hours and diluted with 600 ml of hexanes. The reaction mixture was filtered and the filtrate stirred with 500 ml of a saturated Na$_2$SO$_3$ solution for 3 hours. The organic layer was separated, washed well with water, dried and evaporated in vacuo to give 12 gm of a semi-solid.

EXAMPLE 24

2-(4-Methoxy-benzenesulfonyl)-2-methyl-3-[4-(2-piperidin-1-yl-ethoxy)-phenyl]propionic acid ethyl ester

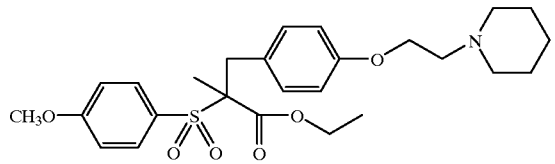

To a stirred mixture of 2.7 g (10 mmol) of 2-(4-methoxy-benzenesulfonyl)propionic acid ethyl ester, 3.03 gm (10 mmol) 4-(2-piperidin-1-yl-ethoxy)benzyl chloride, 10 gm of K$_2$CO$_3$ and 500 mg of 18-crown-6 in 250 ml of acetone was refluxed for 16 hours. At the end, the reaction mixture was filtered and the acetone layer was concentrated to a residue.

The residue was extracted with chloroform, washed well with water, dried over anhydrous MgSO$_4$, filtered and concentrated to a residue. The residue obtained was purified by silica-gel column chromatography by eluting with 50% ethyl acetate-hexanes to afford 4.8 gm (92%) of the desired product as an oil. MS: 490(M+H)$^+$.

EXAMPLE 25

2-(4-Methoxybenzenesulfonyl)-2-methyl-3-[4-(2-piperidinyl-1-yl-ethoxy)-phenyl]-propionic acid

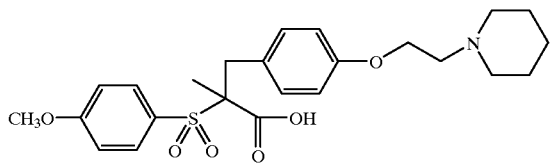

To a stirred solution of 2-(4-methoxybenzenesulfonyl)-2-methyl-3-[4-(2-piperidin-1-yl-ethoxy)phenyl]propionic acid ethyl ester (4.9 gm, 10 mmol) in methyl alcohol was added 10 N NaOH (20 ml, excess). The reaction mixture was stirred at room temperature for 48 hours. At the end, the reaction mixture was concentrated and carefully neutralized with dilute HCl. The residue obtained was extracted with chloroform, washed well with water, dried and concentrated. The product obtained was purified by silica gel column chromatography by eluting with ethyl acetate:methanol (95:5) to afford the product of the example as colorless crystals, m.p. 106° C.; MS: 462.5 (M+H)$^+$. Yield 4.1 gm, 88–1.

EXAMPLE 26

2-(4-Methoxybenzenesulfonyl)-2-methyl-3-[4-(2-piperidin-1-yl-ethoxy)-phenyl]-propionamide

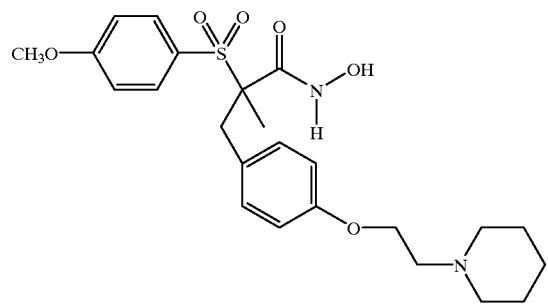

To a stirred solution of 2-(4-methoxy-phenylsulfonyl)-2-methyl-3-phenyl-[4-(2-piperidin-1-yl-ethoxy)]propionic acid (2.3 g, 5 mmol) of DMF (2 drops) in CH$_2$Cl$_2$ (100 ml) at 0° C., oxalyl chloride (1.2 gm, 10 mmol) was added in a dropwise manner. After the addition, the reaction mixture was stirred at room temperature for 1 hour. Simultaneously, in a separate flask a mixture of hydroxylamine hydrochloride (3.4 gm, 50 mmol) of triethylamine (10.1 gm, 100 mmol) was stirred in THF:water (5:1, 50 ml) at 0° C. for 1 hour. At the end of 1 hour, the oxalyl chloride reaction mixture was concentrated and the pale yellow residue was dissolved in 10 ml of CH$_2$Cl$_2$ and added slowly to the hydroxylamine at 0° C. The reaction mixture was stirred at room temperature for 24 hours and concentrated. The residue obtained was extracted with chloroform and washed well with water. The product obtained was purified by silica gel column chromatography and eluted with ethyl acetate. The product of the example was isolated as a colorless solid. mp 98° C.; Yield, 48%; MS: 477 (M+H)$^+$; 1H NMR (300 MHz, CDCl3): _1.2 (s, 3H), 3.5–1.5 (m, 16H), 3.9 (s, 3H), 4.4 (m, 1H); 6.5–7.8 (m, 8H); 10.8 (bs, 1H).

The subject compounds of the present invention were tested for biological activity according to the following procedures.

In Vitro Gelatinase Assay

The assay is based on the cleavage of the thiopeptide substrate ((Ac-Pro-Leu-Gly(2 mercapto-4 methyl-pentanoyl)-Leu-Gly-OEt), Bachem Bioscience) by the enzyme, gelatinase, releasing the substrate product which reacts calorimetrically with DTNB ((5,5'-dithio-bis(2-nitrobenzoic acid)). The enzyme activity is measured by the rate of the color increase. The thiopeptide substrate is made up fresh as a 20 mM stock in 100% DMSO and the DTNB is dissolved in 100% DMSO as a 100 mM stock and stored in dark at room temperature. Both the substrate and DTNB are diluted together to 1 mM with substrate buffer (50 mM HEPES pH 7.5, 5 mM CaCl$_2$) before use. The stock of human neutrophil gelatinase B is diluted with assay buffer (50 mM HEPES pH 7.5, 5 mM CaCl$_2$, 0.02% Brij) to a final concentration of 0.15 nM. The assay buffer, enzyme, DTNB/substrate (500 µM final concentration) and vehicle or inhibitor are added to a 96 well plate (total reaction volume of 200 µl) and the increase in color is monitored spectrophotometrically for 5 minutes at 405 nm on a plate reader. The increase in OD$_{405}$ is plotted and the slope of the line is calculated which represents the reaction rate. The linearity of the reaction rate is confirmed ($r^2$>0.85). The mean (x±sem) of the control rate is calculated and compared for statistical significance (p<0.05) with drug-treated rates using Dunnett's multiple comparison test. Dose-response relationships can be generated using multiple doses of drug and IC$_{50}$ values with 95% CI are estimated using linear regression (IPRED, HTB).
References: Weingarten, H and Feder, J., Spectrophotometric assay for vertebrate collagenase, Anal. Biochem. 147, 437440 (1985).

In Vitro Collagenase Assay

The assay is based on the cleavage of a peptide substrate ((Dnp-Pro-Cha-Gly-Cys(Me)-His-Ala-Lys(NMa)-NH$_2$), Peptide International, Inc.) by collagenase releasing the fluorescent NMa group which is quantitated on the fluorometer. Dnp quenches the NMa fluorescence in the intact substrate. The assay is run in HCBC assay buffer (50 mM HEPES, pH 7.0, 5 mM Ca$^{+2}$, 0.02% Brij, 0.5% Cysteine), with human recombinant fibroblast collagenase (truncated, mw=18,828, WAR, Radnor). Substrate is dissolved in methanol and stored frozen in 1 mM aliquots. Collagenase is stored frozen in buffer in 25 µM aliquots. For the assay, substrate is dissolved in HCBC buffer to a final concentration of 10 µM and collagenase to a final concentration of 5 nM. Compounds are dissolved in methanol, DMSO, or HCBC. The methanol and DMSO are diluted in HCBC to <1.0%. Compounds are added to the 96 well plate containing enzyme and the reaction is started by the addition of substrate. The reaction is read (excitation 340 nm, emission 444 nm) for 10 min. and the increase in fluorescence over time is plotted as a linear line. The slope of the line is calculated and represents the reaction rate. The linearity of the reaction rate is confirmed ($r^2$>0.85). The mean (x±sem)

of the control rate is calculated and compared for statistical significance (p<0.05) with drug-treated rates using Dunnett's multiple comparison test. Dose-response relationships can be generated using multiple doses of drug and IC$_{50}$ values with 95% CI are estimated using linear regression (IPRED, HTB). References: Bickett, D. M. et al., A high throughput fluorogenic substrate for interstitial collagenase (MMP-1) and gelatinase (MMP-9), Anal. Biochem. 212, 58–64 (1993).

Procedure for Measuring TACE Inhibition

Using 96-well black microtiter plates, each well receives a solution composed of 10 μL TACE (Immunex, final concentration 1 μg/mL), 70 μL Tris buffer, pH 7.4 containing 10% glycerol (final concentration 10 mM), and 10 μL of test compound solution in DMSO (final concentration 1 μM, DMSO concentration<1%) and incubated for 10 minutes at room temperature. The reaction is initiated by addition of a fluorescent peptidyl substrate (final concentration 100 μM) to each well and then shaking on a shaker for 5 sec. The reaction is read (excitation 340 nm, emission 420 nm) for 10 min. and the increase in fluorescence over time is plotted as a linear line. The slope of the line is calculated and represents the reaction rate. The linearity of the reaction rate is confirmed ($r^2$>0.85). The mean (x±sem) of the control rate is calculated and compared for statistical significance (p<0.05) with drug-treated rates using Dunnett's multiple comparison test. Dose-response relationships can be generate using multiple doses of drug and IC$_{50}$ values with 95% CI are estimated using linear regression.

The results obtained following these standard experimental test procedures are presented in the following table.

| | IC 50 (nM or % inhibition at 1 micromolar) | | | |
|---|---|---|---|---|
| Example | MMP 1 | MMP 9 | MMP 13 | TACE |
| 26 | 238.6 | 8.9 | 1.4 | 41.00% |

Procedures for Measuring MMP-1, MMP-9, and MMP-13 Inhibition

These assays are based on the cleavage of a thiopeptide substrates such as Ac-Pro-Leu-Gly(2-mercapto4-methyl-pentanoyl)-Leu-Gly-OEt by the matrix metalloproteinases MMP-1, MMP-13 (collagenases) or MMP-9 (gelatinase), which results in the release of a substrate product that reacts calorimetrically with DTNB (5,5'-dithiobis(2-nitro-benzoic acid)). The enzyme activity is measured by the rate of the color increase. The thiopeptide substrate is made up fresh as a 20 mM stock in 100% DMSO and the DTNB is dissolved in 100% DMSO as a 100 mM stock and stored in the dark at room temperature. Both the substrate and DTNB ate diluted together to 1 mM with substrate buffer (50 mM HEPES pH 7.5, 5 mM CaCl$_2$) before use. The stock of enzyme is diluted with assay buffer (50 mM HEPES, pH 7.5, 5 mM CaCl$_2$, 0.02% Brij) to the desired final concentration. The assay buffer, enzyme, vehicle or inhibitor, and DTNB/substrate are added in this order to a 96 well plate (total reaction volume of 200 μl) and the increase in color is monitored spectrophotometrically for 5 minutes at 405 nm on a plate reader and the increase in color over time is plotted as a linear line.

Alternatively, a fluorescent peptide substrate is used. In this assay, the peptide substrate contains a fluorescent group and a quenching group. Upon cleavage of the substrate by an MMP, the fluorescence that is generated is quantitated on the fluorescence plate reader. The assay is run in HCBC assay buffer (50 mM HEPES, pH 7.0, 5 mM Ca$^{+2}$, 0.02% Brij, 0.5% Cysteine), with human recombinant MMP-1, MMP-9, or MMP-13. The substrate is dissolved in methanol and stored frozen in 1 mM aliquots. For the assay, substrate and enzymes are diluted in HCBC buffer to the desired concentrations. Compounds are added to the 96 well plate containing enzyme and the reaction is started by the addition of substrate. The reaction is read (excitation 340 nm, emission 444 nm) for 10 min. and the increase in fluorescence over time is plotted as a linear line.

For either the thiopeptide or fluorescent peptide assays, the slope of the line is calculated and represents the reaction rate. The linearity of the reaction rate is confirmed ($r^2$>0.85). The mean (x±sem) of the control rate is calculated and compared for statistical significance (p<0.05) with drug-treated rates using Dunnett's multiple comparison test. Dose-response relationships can be generated using multiple doses of drug and IC$_{50}$ values with 95% CI are estimated using linear regression.

In vivo MMP Inhibition

A 2 cm piece of dialysis tubing (molecular weight cut-off 12–14,000, 10 mm flat width) containing matrix metalloproteinase enzyme (stromelysin, collagenase or gelatinase in 0.5 mL of buffer) is implanted either ip or sc (in the back) of a rat (Sprague-Dawley, 150–200 g) or mouse (CD-1, 25–50 g) under anesthesia. Drugs are administered PO, IP, SC or IV through a canula in the jugular vein. Drugs are administered in a dose volume of 0.1 to 0.25 mL/animal. Contents of the dialysis tubing is collected and enzyme activity assayed.

Enzyme reaction rates for each dialysis tube are calculated. Tubes from at least 3 different animals are used to calculate the mean±sem. Statistical significance (p<0.05) of vehicle-treated animals versus drug-treated animals is determined by analysis of variance. (*Agents and Actions* 21: 331, 1987).

Procedure for Measuring TACE Inhibition

Using 96-well black microtiter plates, each well receives a solution composed of 10 μL TACE (Immunex, final concentration 1 μg/mL), 70 μL Tris buffer, pH 7.4 containing 10% glycerol (final concentration 10 mM), and 10 μL of test compound solution in DMSO (final concentration 1 μM, DMSO concentration <1%) and incubated for 10 minutes at room temperature. The reaction is initiated by addition of a fluorescent peptidyl substrate (final concentration 100 μM) to each well and then shaking on a shaker for 5 sec.

The reaction is read (excitation 340 nm, emission 420 nm) for 10 min. and the increase in fluorescence over time is plotted as a linear line. The slope of the line is calculated and represents the reaction rate.

The linearity of the reaction rate is confirmed ($r^2$>0.85). The mean (x±sem) of the control rate is calculated and compared for statistical significance (p<0.05) with drug-treated rates using Dunnett's multiple comparison test. Dose-response relationships can be generate using multiple doses of drug and IC$_{50}$ values with 95% CI are estimated using linear regression.

Results of the above in-vitro and in-vivo matrix metalloproteinase inhibition and TACE inhibition pharmacological assays are given in Table I below.

TABLE I

Inhibition of MMP and TACE

| Example | MMP-1[1] | MMP-9[1] | MMP-13[1] | in-vivo MMP[2] | TACE[1] |
|---------|----------|----------|-----------|----------------|---------|
| 20 | 176 | 6.9 | 56 | | 277 |
| 21 | 96 | 2.3 | 8.8 | | 215 |

[1]IC$_{50}$ nM or % inhibition at 1 µM concentration
[2]% inhibition vs. MMP-9 (dose, mg/kg), ip = intraperitoneal, po = oral

What is claimed:

1. A process for the production of a compound of the formula:

$$Y-(C)_m(R^1)(R^2)-C(R^1)(R^2)-O-\text{Ar}(R^3,R^4,R^5,R^6)-C(R^1)(R^2)-X$$

wherein:

$R^1$ and $R^2$ are, independently, selected from H; $C_1$–$C_{12}$ alkyl or $C_1$–$C_6$ perfluorinated alkyl;

X selected from halogen, —O—SO$_2$—CH$_3$, —O—SO$_2$—CF$_3$, or a moiety of the structure:

$$-O-S(=O)_2-\text{C}_6\text{H}_4-Z;$$

Z is —NO$_2$, halogen, —CH$_3$ or —CF$_3$;

m is an integer from 0 to 3;

$R^3$, $R^4$, $R^5$, and $R^6$ are independently selected from H, halogen, —NO$_2$, alkyl, alkoxy, $C_1$–$C_6$ perfluorinated alkyl, OH or the $C_1$–$C_4$ esters or alkyl ethers thereof, —CN, —O—$R^1$, —O—Ar, —S—$R^1$, —S—Ar, —SO—$R^1$, —SO—Ar, —SO$_2$—$R^1$, —SO$_2$—Ar, —CO—$R^1$, —CO—Ar, —CO$_2$—$R^1$, or —CO$_2$—Ar; and Y is a six-membered saturated, unsaturated or partially unsaturated heterocycle containing up to two heteroatoms selected from the group consisting of —O—, —NH—, —N(C$_1$C$_4$ alkyl)—, —N═, and —S(O)$_n$—, wherein n is an integer of from 0–2, substituted or unsubstituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, phenyl substituted or unsubstituted with 1–3 ($C_1$–$C_4$)alkyl, —CO$_2$H, —CN, —CONHR$^1$, —NH$_2$, $C_1$–$C_4$ alkylamino, $C_1$–$C_4$ dialkylamino, —NHSO$_2$R$^1$, —NHCOR$^1$, or —NO$_2$;

the process comprising the steps of:
a) alkylating a hydroxybenzaldehyde of the formula:

$$HO-\text{Ar}(R^3,R^4,R^5,R^6)-CHO$$

wherein $R^3$–$R^6$ are as defined above, with an alkyl halide of the formula:

$$Y-(C)_m(R^1)(R^2)-C(R^1)(R^2)-\text{halo}$$

wherein $R^1$, $R^2$ and Y are as defined above, m is an integer from 0 to 3 and halo is Cl, F, Br or I, to produce an aldehyde of the formula:

$$Y-(C)_m(R^1)(R^2)-C(R^1)(R^2)-O-\text{Ar}(R^3,R^4,R^5,R^6)-CHO;$$

b) reducing the aldehyde product of step a), to yield an alcohol of the formula:

$$Y-(C)_m(R^1)(R^2)-C(R^1)(R^2)-O-\text{Ar}(R^3,R^4,R^5,R^6)-CH_2OH$$

c) converting the alcohol of step b) to its hydrochloride salt; and d) converting the alcohol group in the compound of step c) to a leaving group.

2. A process of claim 1 wherein halo is Cl, m is 2 and the alcohol is converted to a leaving group through reacting with methanesulfonyl chloride, toluenesulfonyl chloride, or trifluoroacetic anhydride in the presence of pyridine or triethylamine.

3. A process of claim 2 wherein the compound has the formula:

$$Y-(C)_m(R^1)(R^2)-C(R^1)(R^2)-A-\text{Ar}(R^3,R^4,R^5,R^6)-C(R^1)(R^2)-X \quad (I)$$

wherein:

$R^1$ and $R^2$ are, independently, selected from H; $C_1$–$C_{12}$ alkyl or $C_1$–$C_6$ perfluorinated alkyl;

$R^3$, $R^4$, $R^5$, and $R^6$ are as defined above;

X is halogen, —O—SO$_2$—CH$_3$, —O—SO$_2$—CF$_3$, or a moiety of the structure:

$$-O-\underset{\underset{O}{\|}}{\overset{\overset{O}{\|}}{S}}-\underset{}{\underset{}{\bigcirc}}-Z;$$

Z is —NO$_2$, halogen, —CH$_3$ or —CF$_3$;

A is —O—;

m is an integer from 0 to 3; and

Y is selected from the group of pyridine, pyrazine, pyrimidine, pyridazine or piperidine, the group being substituted or unsubstituted with 1–3 substituents independently selected from the group consisting of hydrogen, hydroxyl, halo, C$_1$-C$_4$ alkyl, trihalomethyl, C$_1$-C$_4$ alkoxy, trihalomethoxy, C$_1$-C$_4$ acyloxy, C$_1$-C$_4$ alkylthio, C$_1$-C$_4$ alkylsulfinyl, C$_1$-C$_4$ alkylsulfonyl, hydroxy (C$_1$-C$_4$)alkyl, phenyl substituted or unsubstituted with 1–3 (C$_1$-C$_4$)alkyl, —CO$_2$H, —CN, —CONHR$^1$, —NH$_2$, C$_1$-C$_4$ alkylamino, C$_1$-C$_4$ dialkylamino, —NHSO$_2$R$^1$, —NHCOR$^1$, —NO$_2$; or a pharmaceutically acceptable salt thereof.

4. A process of claim 1 wherein:

R$^1$ and R$^2$ are independently selected from H, C$_1$-C$_6$ alkyl or C$_1$-C$_6$ perfluorinated alkyl;

R$^3$, R$^4$, R$^5$, and R$^6$ are independently selected from H, OH or the C$_1$-C$_4$ esters or alkyl ethers thereof, halogen, —CN, C$_1$-C$_6$ alkyl, or trifluoromethyl;

m is an integer from 0 to 3;

Y is selected from the group of pyridine, pyrazine, pyrimidine, pyridazine or piperidine, the group being substituted or unsubstituted with 1–3 substituents independently selected from the group consisting of hydrogen, hydroxyl, halo, C$_1$-C$_4$ alkyl, trihalomethyl, C$_1$-C$_4$ alkoxy, trihalomethoxy, C$_1$-C$_4$ acyloxy, C$_1$-C$_4$ alkylthio, C$_1$-C$_4$ alkylsulfinyl, C$_1$-C$_4$ alkylsulfonyl, hydroxy (C$_1$-C$_4$)alkyl, phenyl substituted or unsubstituted with 1–3 (C$_1$-C$_4$)alkyl, —CO$_2$H, —CN, —CONHR$^1$, —NH$_2$, C$_1$-C$_4$ alkylamino, C$_1$-C$_4$ dialkylamino, —NHSO$_2$R$^1$, —NHCOR$^1$, —NO$_2$; and X is halogen, —O—SO$_2$—CH$_3$, —O—SO$_2$—CF$_3$, or a moiety of the structure:

$$-O-\underset{\underset{O}{\|}}{\overset{\overset{O}{\|}}{S}}-\underset{}{\underset{}{\bigcirc}}-Z;$$

and Z is selected from —NO$_2$, halogen, —CH$_3$ or —CF$_3$.

5. A process of claim 1 wherein the compound is (4-Chloromethyl-phenoxy)-ethyl-piperidin-1-yl hydrochloride.

6. A process of claim 1 wherein the compound is (4-Chloromethyl-phenoxy)-ethyl-hexamethyleneimine-1-yl hydrochloride.

7. A process for the production of compounds of the formula:

$$Y-(\underset{R^2}{\overset{R^1}{C}})_m-\underset{R^2}{\overset{R^1}{C}}-S-\underset{R^5}{\overset{R^3}{\underset{}{\bigcirc}}}\overset{R^1}{\underset{R^6}{\overset{R^2}{C}}}-X$$

wherein:

R$^1$ and R$^2$ are, independently, selected from H; C$_1$-C$_{12}$ alkyl or C$_1$-C$_6$ perfluorinated alkyl;

X selected from halogen, —O—SO$_2$—CH$_3$, —O—SO$_2$—CF$_3$, or a moiety of the structure:

$$-O-\underset{\underset{O}{\|}}{\overset{\overset{O}{\|}}{S}}-\underset{}{\underset{}{\bigcirc}}-Z;$$

Z is —NO$_2$, halogen, —CH$_3$ or —CF$_3$;

m is an integer from 0 to 3;

R$^3$, R$^4$, R$^5$, and R$^6$ are independently selected from H, halogen, —NO$_2$, alkyl, alkoxy, C$_1$-C$_6$ perfluorinated alkyl, OH or the C$_1$-C$_4$ esters or alkyl ethers thereof, —CN, —O—R$^1$, —O—Ar, —S—R$^1$, —S—Ar, —SO—R$^1$, —SO—Ar, —SO$_2$—R$^1$, —SO$_2$—Ar, —CO—R$^1$, —CO—Ar, —CO$_2$—R$^1$, or —CO$_2$—Ar; and Y is a six-membered saturated, unsaturated or partially unsaturated heterocycle containing up to two heteroatoms selected from the group consisting of —O—, —NH—, —N(C$_1$C$_4$ alkyl)—, —N=, and —S(O)$_n$—, wherein n is an integer of from 0–2, substituted or unsubstituted with 1–3 substituents independently selected from the group consisting of hydrogen, hydroxyl, halo, C$_1$-C$_4$ alkyl, trihalomethyl, C$_1$-C$_4$ alkoxy, trihalomethoxy, C$_1$-C$_4$ acyloxy, C$_1$-C$_4$ alkylthio, C$_1$-C$_4$ alkylsulfinyl, C$_1$-C$_4$ alkylsulfonyl, hydroxy (C$_1$-C$_4$)alkyl, phenyl substituted or unsubstituted with 1–3 (C$_1$-C$_4$)alkyl, —CO$_2$H, —CN, —CONHR$^1$, —NH$_2$, C$_1$-C$_4$ alkylamino, C$_1$-C$_4$ dialkylamino, —NHSO$_2$R$^1$, —NHCOR$^1$, or —NO$_2$;

the process comprising the steps of:

a) alkylating a compound of the following formula:

$$HS-\underset{R^5}{\overset{R^3}{\underset{}{\bigcirc}}}\overset{}{\underset{R^6}{\overset{R^4}{C}}}-CHO$$

wherein R$^3$–R$^6$ are as defined above, with an alkylating agent of the formula:

$$Y-(\underset{R^2}{\overset{R^1}{C}})_m-\underset{R^2}{\overset{R^1}{C}}-halo$$

wherein Y and m are as defined above, to produce an aldehyde of the formula:

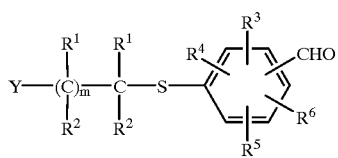

b) reducing the aldehyde to an alcohol of the formula;

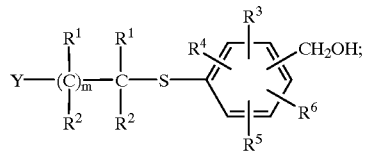

c) reacting with the alcohol of step b) with gaseous HCl to generate its hydrochloride; and d) converting the alcohol hydrochloride product of step c) to a leaving group.

8. The process of claim 7 further comprising the step of controlled oxidation of the sulfur in the alcohol hydrochloride of step d) to sulfoxide or to sulfone.

9. A process of claim 7 wherein halo is Cl, m is 2 and the alcohol is converted to a leaving group through reacting with methanesulfonyl chloride, toluenesulfonyl chloride, or trifluoroacetic anhydride in the presence of pyridine or triethylamine.

* * * * *

UNITED STATES PATENT AND TRADEMARK OFFICE
CERTIFICATE OF CORRECTION

PATENT NO.     : 6,242,605 B1                                          Page 1 of 1
DATED          : June 5, 2001
INVENTOR(S)    : Panolil Raveendranath et al.

It is certified that error appears in the above-identified patent and that said Letters Patent is hereby corrected as shown below:

Column 14,
Lines 42-45, replace the structure with the following:

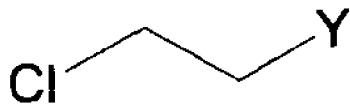

Signed and Sealed this

Twenty-eighth Day of March, 2006

JON W. DUDAS
*Director of the United States Patent and Trademark Office*